US009505778B2

(12) United States Patent
Gallagher et al.

(10) Patent No.: US 9,505,778 B2
(45) Date of Patent: Nov. 29, 2016

(54) MONOMERS, POLYMERS AND ARTICLES CONTAINING THE SAME FROM SUGAR DERIVED COMPOUNDS

(71) Applicant: REGENTS OF THE UNIVERSITY OF MINNESOTA, Minneapolis, MN (US)

(72) Inventors: James Gallagher, Minneapolis, MN (US); Theresa Reineke, Vadnais Heights, MN (US); Marc A. Hillmyer, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 90 days.

(21) Appl. No.: 14/554,823

(22) Filed: Nov. 26, 2014

(65) Prior Publication Data

US 2015/0148507 A1 May 28, 2015

Related U.S. Application Data

(60) Provisional application No. 61/909,475, filed on Nov. 27, 2013.

(51) Int. Cl.
*C08F 222/22* (2006.01)
*A61K 47/32* (2006.01)
*C07D 493/04* (2006.01)
*A61K 47/34* (2006.01)
*C08F 222/10* (2006.01)

(52) U.S. Cl.
CPC ............ *C07D 493/04* (2013.01); *A61K 47/34* (2013.01); *C08F 222/1006* (2013.01)

(58) Field of Classification Search
CPC ................ A61K 47/34; C07D 493/04; C08F 222/1006
USPC ......................................... 526/270; 549/304
See application file for complete search history.

(56) References Cited

U.S. PATENT DOCUMENTS

2005/0267280 A1 12/2005 Ignatious

FOREIGN PATENT DOCUMENTS

WO  WO 96/36890 A1  11/1996
WO  WO 2005/082978 A1  9/2005

OTHER PUBLICATIONS

Hashimoto et al. (Macromolecular synthesis from saccharic lactones. Polyaddition of D-glucaro- and D-mannaro-1,4:6,3-dilactones with Diisocyanates and Hydrolyzability of the Resulting Polyurethanes Having Dilactone Rings in the Main Chains, Journal of Polymer Science: Part A Polymer Chemistry, vol. 33, 1495-1503, 1995).*
Andrzejewska, "Photopolymerization kinetics of multifunctional monomers," *Prog. Polym. Sci.*, May 2001; 26(4):605-665.
Anseth et al., "Polymerizations of Multifunctional Anhydride Monomers to Form Highly Crosslinked Degradable Networks," *Macromol. Rapid Commun.*, May 2001; 22(8):564-572.
Barszczewska-Rybarek et al., "Evaluation of the network parameter in aliphatic poly(urethane dimethacrylate)s by dynamic thermal analysis," *Polymer*, Apr. 2000; 41(9):3129-3135.
Bowman et al., "Coupling of kinetics and volume relaxation during polymerizations of multiacrylates and multimethacrylates," *Macromolecules*, Apr. 1991; 24(8):1914-1920.
De Clercq et al., "Polymer networks containing degradable polyacetal segments," *Macromolecules*, Feb. 1992; 25(3):1109-1113.
Downey et al., "Growth Mechanism of Poly(divinylbenzene) Microspheres in Precipitation Polymerization," *Macromolecules*, Apr. 1999; 32(9):2838-2844.
Elsabahy et al., "Design of polymeric nanoparticles for biomedical delivery applications," *Chem. Soc. Rev.*, Apr. 2012; 41(7):2545-2561 (Published online Feb. 14, 2012).
Feng et al., "Sugar-Based Chemicals for Environmentally Sustainable Applications," *Contemporary Science of Polymeric Materials; ACS Symposium Series*, Chapter 1; Washington, D.C.; Dec. 14, 2010: 25 pgs.
Fenouillot et al., "Polymers from renewable 1,4:3,6-dianhydrohexitols (isosorbide, isomannide and isoidide): A review," *Prog. Polym. Sci.* 2010, 35(5):578-622 (Available online Oct. 30, 2009).
Fu et al., "Hollow polymeric nanostructures—Synthesis, morphology and function," *Prog. Polym. Sci.*, Jan. 2011; 36(1):127-167.
Gallagher et al., "Thermoset Material from a Glucose-based Dimethacrylate," *Center for Sustainable Polymers Annual Meeting*, poster and presentation; Apr. 18, 2013: 1 pg.
Gallagher et al., "Thermoset Materials from Sugar Derived Dilactones," *IPRIME Meeting*, presentation; May 30, 2013: 21 pgs . . . .
Gallagher et al., "Degradable Thermosets from Sugar-Derived Dilactones," *Macromolecules*, Jan. 2014; 47(2):498-505.
Gandini, "The irruption of polymers from renewable resources on the scene of macromolecular science and technology," *Green Chemistry*, 2011; 13(5):1061-1083.
Gehret et al., "Convenient Large-Scale Synthesis of d-Glucaro-1,4:6,3-dilactone," *J. Org. Chem.*, Nov. 2009; 74(21):8373-8376 (Published online Sep. 24, 2009).
Hashimoto et al., "Ring-opening polyaddition of D-glucaro-1,4:6,3-dilactone with p-xylylenediamine," *Makromol. Chem. Rapid Commun.*, Aug. 1990; 11(8):393-396.
Hashimoto et al., "Macromolecular synthesis from saccharic lactones. Ring-opening polyaddition of D-glucaro- and D-mannaro-1,4:6,3-dilactones with alkylenediamines," *J. Polym. Sci. A. Polym. Chem.*, Nov. 1993; 31(12) :3141-3149.

(Continued)

*Primary Examiner* — Ling Choi
*Assistant Examiner* — Chun-Cheng Wang
(74) *Attorney, Agent, or Firm* — Mueting, Raasch & Gebhardt, P.A.

(57) ABSTRACT

Disclosed herein are monomers formed by reacting a sugar derived compound(s) comprising a lactone and two hydroxyls with a compound(s) comprising an isocyanate and an acrylate or methacrylate. Polymers formed from such monomers, and articles formed from the polymers are also disclosed.

20 Claims, 11 Drawing Sheets

(56) References Cited

OTHER PUBLICATIONS

Hashimoto et al., "Macromolecular synthesis from saccharic lactones. Polyaddition of D-glucaro- and D-mannaro-1,4:6, 3-dilactones with diisocyanates and hydrolyzability of the resulting polyurethanes having dilactone rings in the main chains," *J. Polym. Sci. A. Polym. Chem.*, Jul. 1995; 33(9):1495-1503.

Jiang et al., "Narrow or Monodisperse, Highly Cross-Linked, and "Living" Polymer Microspheres by Atom Transfer Radical Precipitation Polymerization," *Macromolecules*, Aug. 2011; 44(15):5893-5904 (Published online Jul. 15, 2011).

Kiely et al., "Hydroxylated nylons based on unprotected esterified D-glucaric acid by simple condensation reactions," *J. Am. Chem. Soc.*, Jan. 1994; 116(2):571-578.

Kiely et al., "Synthetic polyhydroxypolyamides from galactaric, xylaric, D-glucaric, and D-mannaric acids and alkylenediamine monomers—some comparisons," *J. Polym. Sci. Part A: Polym. Chem.*, Feb. 2000; 38(3):594-603 (Published online Jan. 21, 2000).

Kim et al., "Hydrogen-Bonding Layer-by-Layer-Assembled Biodegradable Polymeric Micelles as Drug Delivery Vehicles from Surfaces," *ACS Nano*, Feb. 2008; 2(2):386-392.

Kloosterboer, "Network formation by chain crosslinking photopolymerization and its applications in electronics," *Adv. Polym. Sci.* 1988, 84:1-61.

Kurdikar et al., "A Kinetic Model for Diffusion-Controlled Bulk Crosslinking Photopolymerizations," *Macromolecules*, 1994; 27(15):4084-4092.

Li et al . . . , "Porous monodisperse poly(divinylbenzene) microspheres by precipitation polymerization," *J. Polym. Sci. A. Polym. Chem.*, Jul. 1998; 36(10):1543-1551.

Li et al., "Mono- or narrow disperse poly(methacrylate-co-divinylbenzene) microspheres by precipitation polymerization," *J. Polym. Sci. A. Polym. Chem.*, Aug. 1, 1999; 37(15):2899-2907.

Li et al. "Monodisperse Cross-Linked Core-Shell Polymer Microspheres by Precipitation Polymerization," *Macromolecules*, Jun. 2000; 33(12):4354-4360.

Li et al., "Facile Synthesis of Hollow Polymer Microspheres with Movable Cores with the Aid of Hydrogen-Bonding Interaction," *J. Phys. Chem. B.*, Nov. 2007; 111(44):12781-12786 (Published online Oct. 18, 2007).

Li et al., "Precipitation polymerization for fabrication of complex core-shell hybrid particles and hollow structures," *Chem. Soc. Rev.*, Apr. 21, 2013; 42(8):3628-3646. (Available online Feb. 15, 2013).

Lichtenthaler, "Carbohydrates as organic raw materials," *Ullmann's Encyclopedia of Industrial Chemistry*, 2010; vol. 6: 583-616.

Liu et al., "Hydroxyl Stereochemistry and Amine Number within Poly(glycoamidoamine)s Affect Intracellular DNA Delivery," *J. Am. Chem. Soc.*, Mar. 9, 2005; 127(9):3004-3015. (Available online Feb. 2005).

Liu et al., "Degradation of Poly(glycoamidoamine) DNA Delivery Vehicles: Polyamide Hydrolysis at Physiological Conditions Promotes DNA Release," *Biomacromolecules*, Feb. 2010; 11(2):316-325.

Muggli, "Reaction Behavior of Biodegradable, Photo-Cross-Linkable Polyanhydrides," *Macromolecules*, May 28, 1998; 31(13)4120-4125.

Ogino et al., "Synthesis and Characterization of Thermally Degradable Polymer Networks," *Chem. Mater.*, Dec. 1998; 10(12):3833-3838 (Published online Nov. 10, 1998).

Palmieri et al., "Design of Reversible Cross-Linkers for Step and Flash Imprint Lithography Imprint Resists," *ACS Nano*, Nov. 2007; 1(4):307-312.

Saracoglu et al., "Synthesis of Monodisperse Glycerol Dimethacrylate-Based Microgel Particles by Precipitation Polymerization," *Ind. Eng. Chem. Res.*, May 2009; 48(10):4844-4851 (Published online Apr. 15, 2009).

Schmitz et al., "Films" *Ullmann's Encyclopedia of Industrial Chemistry*, 2000; vol. 14: 649-676.

Scranton et al., "Polymerization reaction dynamics of ethylene glycol methacrylates and dimethacrylates by calorimetry," *Polymer*, 1992; 33(8):1683-1689.

Sideridou et al., "Effect of chemical structure on degree of conversion in light-cured dimethacrylate-based dental resins," *Biomaterials*, Apr. 2002; 23(8):1819-1829.

Sideridou et al., "Study of water sorption, solubility and modulus of elasticity of light-cured dimethacrylate-based dental resins," *Biomaterials*, Feb. 2003; 24(4):655-665.

Sideridou et al., "Reactivity of Benzoyl Peroxide/Amine System as an Initiator for the Free Radical Polymerization of Dental and Orthopaedic Dimethacrylate Monomers: Effect of the Amine and Monomer Chemical Structure," *Macromolecules*, Mar. 2006; 39(6):2072-2080 (Published online Feb. 18, 2006).

Themistou et al., "Star Polymers and Polymer Networks Containing a Novel, Hydrolyzable Diacetal-Based Dimethacrylate Cross-Linker: Synthesis, Characterization, and Hydrolysis Kinetics," *Macromolecules*, Jun. 7, 2007; 40(14):5231-5234.

Thompson et al., "Chemical degradation of poly(2-aminoethyl methacrylate)," *Polym. Degrad. Stab.*, Aug. 2008; 93(8):1460-1466.

Thorne et al., "Microgel applications and commercial considerations," *Colloid. Polym. Sci.* Apr. 2011, 289(5-6):625-646.

Vlakh et a., "Applications of polymethacrylate-based monoliths in high-performance liquid chromatography," *J. Chromatogr. A.* Mar. 27, 2009; 1216(13):2637-2650.

Werpy et al., *Top Value Added Chemicals from Biomass. Volume I—Results of Screening for Potential Candidates from Sugars and Synthesis Gas*; Pacific Northwest National Laboratory—U.S. Dept. of Energy; Aug. 2004: 76 pgs.

Wibullucksanakul et al., "Swelling behavior and controlled release of new hydrolyzable poly(ether urethane) gels derived from saccharide and L-lysine derivatives and poly(ethylene glycol)," *Macromol. Chem. Phys.*, Jun. 1996; 197(6):1865-1876.

Wibullucksanakul et al., "Hydrolysis and release behavior of hydrolyzable poly(etherurethane) gels derived from saccharide-, L-lysine-derivatives, and poly(propylene glycol)," *Macromol. Chem. Phys.*, Feb. 1997; 198(2):305-319.

* cited by examiner

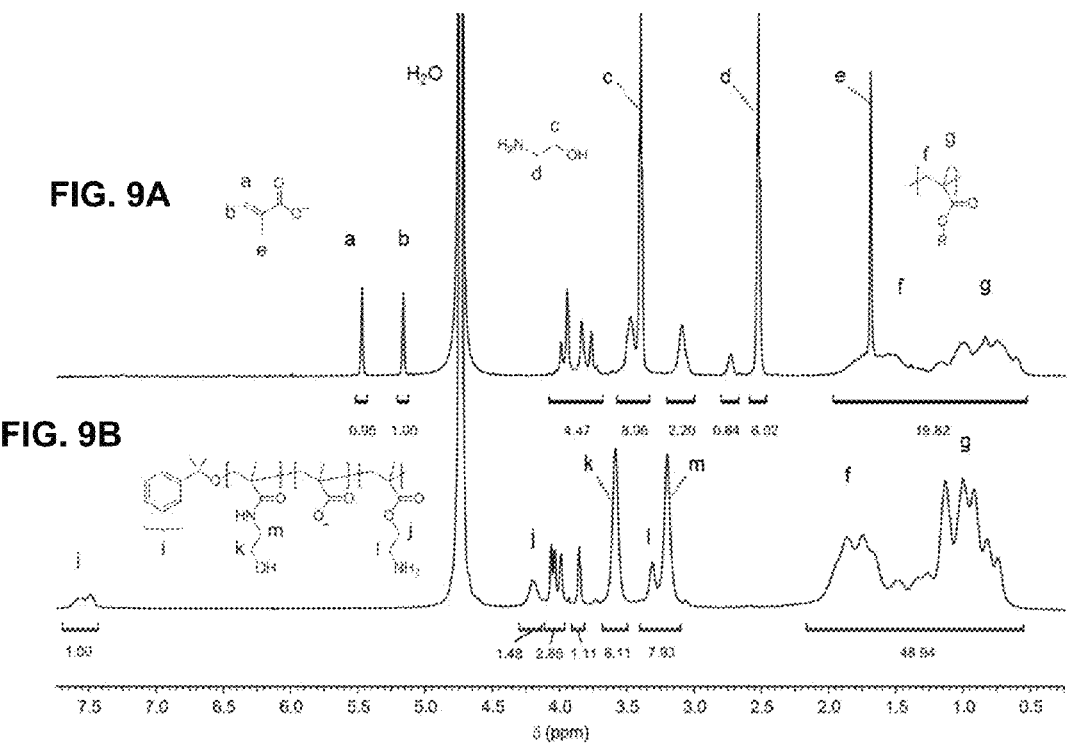
FIG. 9A
FIG. 9B
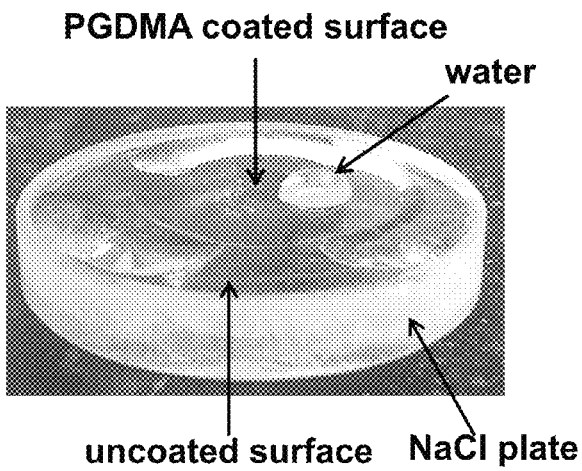
FIG. 10

MONOMERS, POLYMERS AND ARTICLES CONTAINING THE SAME FROM SUGAR DERIVED COMPOUNDS

PRIORITY

This application claims priority to U.S. Provisional Patent Application No. 61/909,475 filed on Nov. 27, 2013 entitled "MONOMERS, POLYMERS AND ARTICLES CONTAINING THE SAME FROM SUGAR DERIVED COMPOUNDS", the entire disclosure of which is incorporated herein by reference thereto.

GOVERNMENT FUNDING

This invention was made with government support under CHE-1136607 awarded by the National Science Foundation. The government has certain rights in the invention.

BACKGROUND

The increased demand and limited supply of petroleum-based chemical feedstocks have spurred a large research push in the area of renewably-sourced polymers. Bio-based feedstocks such as carbohydrates may offer great promise for materials development due to their rich functionality (high heteroatom content and stereochemistry) and renewable production on an impressive scale (~$10^{14}$ kg/yr). Sugars currently comprise a large sector of the chemical industry, with annual production on the order of ~$10^{11}$ kg. Some sugar derivatives are already being touted as viable substitutes for petroleum-based chemicals in polymer applications. For example, isosorbide has been extensively studied in the realm of polymer chemistry and is currently marketed as an alternative to bisphenol A (BPA). Thus, sugars and derivatives thereof are a rich resource for the development of new bio-sourced polymers.

Excellent examples of the unique functionality provided by sugar derivatives are the dilactones glucarodilactone (GDL) and mannarodilactone (MDL). The structure of GDL and MDL are given by formula (I) below.

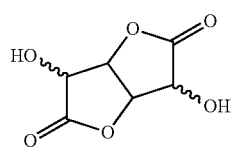

GDL = R, R
MDL = R, S (I)

SUMMARY

Disclosed herein is a compound of formula V below:

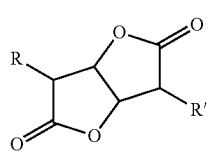

(V)

where R and R' are independently selected from the following:

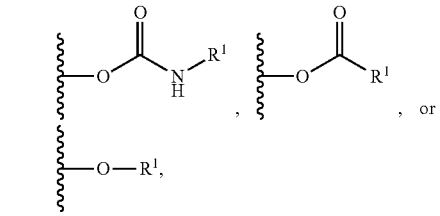

in which $R^1$ is independently selected from:

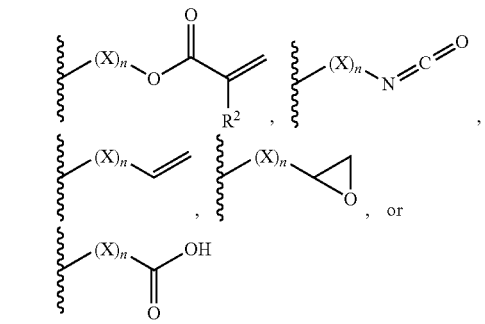

where X is a linking group;
n is an integer greater than or equal to 1; and
$R^2$ is hydrogen, or an alkyl.

Also disclosed is a polymer formed by polymerizing at least a compound of formula V above.

Also disclosed is a drug delivery article including a polymer polymerized from at least a monomer of formula V above.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 9A and 9B show $^1$H-NMR spectra of (FIG. 9A) crude PGDMA degradation products (1 M NaOD, 500 MHz); and (FIG. 9B) high MW degradation products isolated by dialysis (MWCO 3.5 kg/mol) (D$_2$O, 500 MHz).

FIG. 10 is an image of a salt plate containing a PGDMA film (center circle of salt plate). The films derived from these sugar-based feedstocks demonstrate relatively clear and moderately hydrophilic coatings.

Figure 1:
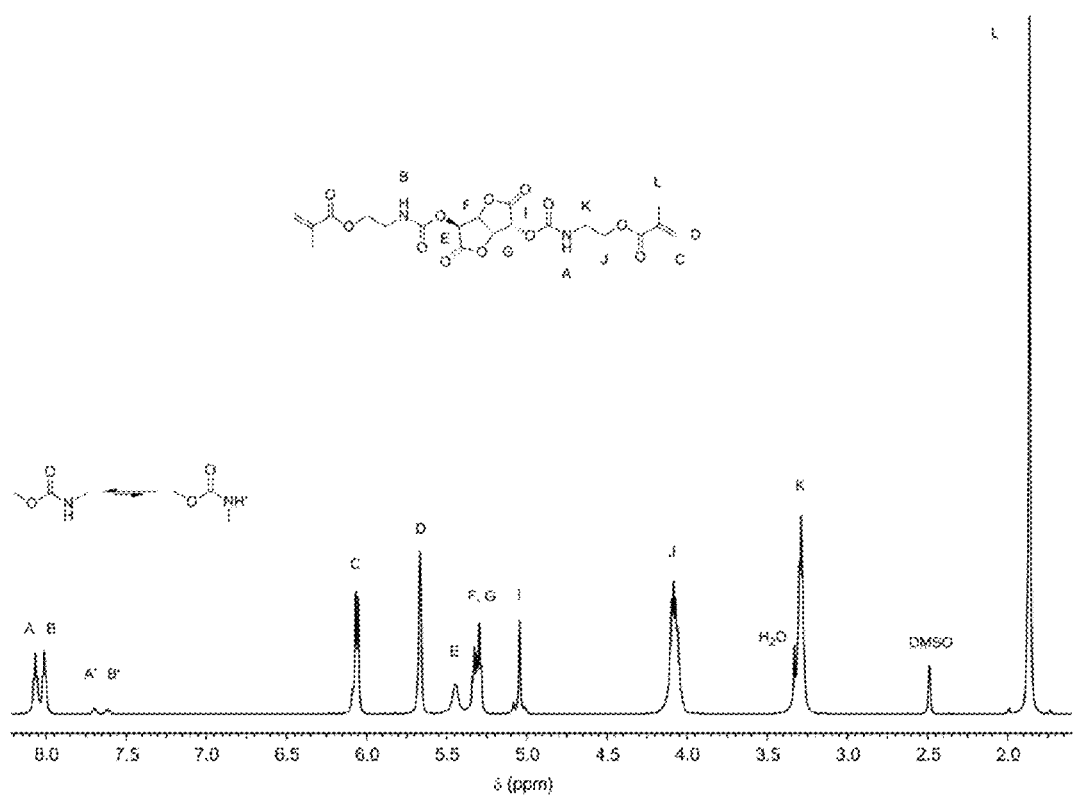
FIG. 1 is a $^1$H-NMR spectrum of GDMA (DMSO-$d_6$, 500 MHz).

Schematic drawings, if present, are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

This disclosure describes, among other things, compounds or monomers that can be derived from, for example, glucose and mannose. Sugar derivatives are renewably sourced, may offer interesting functionality, and may provide rigid ring structures, thus offering the potential to replace BPA and related petroleum-derived structures in thermoset plastics.

Disclosed are compounds or monomers of formula V

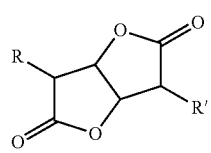

(V)

where R and R' are independently selected from the following:

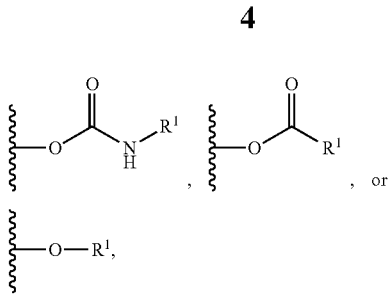

in which $R^1$ is independently selected from: non-reactive groups or reactive groups. Illustrative reactive groups that can be utilized as $R^1$ in R and R' can include

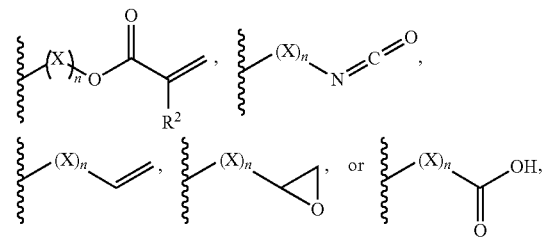

where X is a linking group; n is an integer greater than or equal to one (1) and $R^2$ is hydrogen (H), or an alkyl. Illustrative non-reactive groups can include, for example saturated hydrocarbons, aromatic hydrocarbons, halogenated hydrocarbons, ethers, and esters. In some embodiments, disclosed compounds of formula V include at least one of R and R' that is a reactive group. As such, disclosed compounds of formula V include at least one of R and R' that is one of:

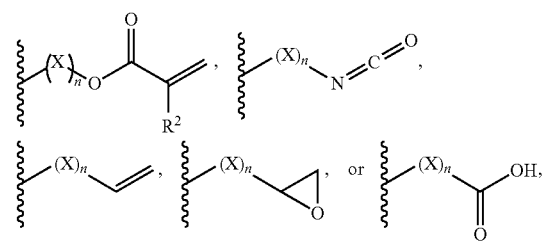

where X, n and $R^2$ are as define above.

In some embodiments, X can be selected from hydrocarbons, esters and ethers for example. In some embodiments X can be a hydrocarbon, and in some embodiments a $C_1$ to $C_6$ alkyl group. In some embodiments, X can be an alkyl containing at least two carbons. In some embodiments X can be a $C_2$ alkyl.

In some embodiments, n can be an integer that is greater than or equal to one (1). In some embodiments, n can be an integer from one (1) to six (6). In some embodiments n can be 1 or 2, and in some embodiments n can be 1.

In some embodiments $R^2$ can be hydrogen (H), or an alkyl. In some embodiments $R^2$ can be H or a $C_1$ to $C_6$ alkyl group, in some embodiments $R^2$ can be H or a $C_1$ to $C_3$ group, and in some embodiments $R^2$ can be H or a $CH_3$ group.

In some embodiments R and R' are both selected from

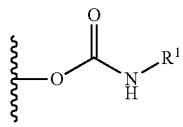

and $R^1$ is

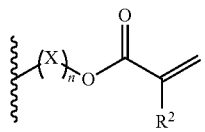

with X independently being a $C_1$ to $C_6$ alkyl group, for example a $C_2$ alkyl group, n being 1 and $R^2$ independently being H or a $C_1$ to $C_3$ alkyl.

Also disclosed are monomers formed by reacting a sugar derived compound(s) comprising a lactone and two hydroxyls with a compound(s) comprising an isocyanate and an acrylate or methacrylate. Furthermore, monomers formed by reacting: at least one compound of formula III with at least one compound of formula IV

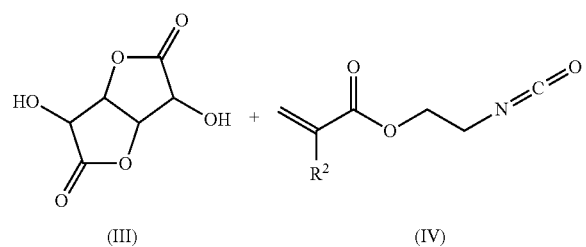

where $R^2$ is H or $CH_3$, are also disclosed. Disclosed monomers can be readily prepared using simple and standard condensation methods in organic solvents, such as tetrahydrofuran, dimethylformamide, or combinations thereof at room temperature.

Specific illustrative examples of disclosed monomers can include, for example dimethacrylate or diacrylate containing monomers, and more specifically glucarodilactone methacrylate (GDMA) and mannarodilactone methacrylate (MDMA). The structures of GDMA and MDMA are shown below as formula VI Disclosed monomers may be synthesized from the sugar derivatives glucarodilactone (GDL) and mannarodilactone (MDL) respectively. This can be advantageous because these sugar derivatives can be sourced from renewable feedstocks, as opposed to non-renewable petroleum resources like other currently utilized dimethacrylates. Disclosed monomers can be described as being derived from, containing, or reacted from GDL, MDL, or some combination thereof. As discussed above, the structure of both GDL and MDL is given by formula I:

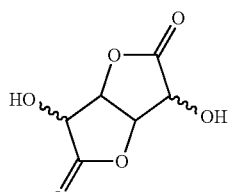

GDL = R, R
MDL = R, S

GDL and MDL can also be more generally described by formula II, which disregards the chirality at the two positions containing the hydroxyl groups.

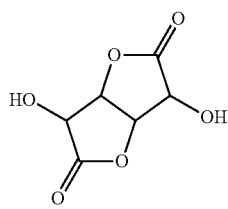

Formula II can describe only GDL, only MDL, or a mixture of GDL and MDL. The chirality of or in compounds disclosed herein will be disregarded and as such formulas presented herein (without an indication of chirality) should be interpreted in a fashion similar to the interpretation of formula II provided in the previous sentence.

GDL and MDL offer advantageous platforms for materials synthesis. These sugar-derived dilactones contain both diol groups to install polymerizable vinyl moieties (i.e. methacrylates) and a unique heteroatom ring system susceptible to further functionalization or degradation.

These molecules, derived from glucose and mannose respectively, are lactone analogues of the dianhydrohexitols isosorbide and isomannide and have been under-utilized in

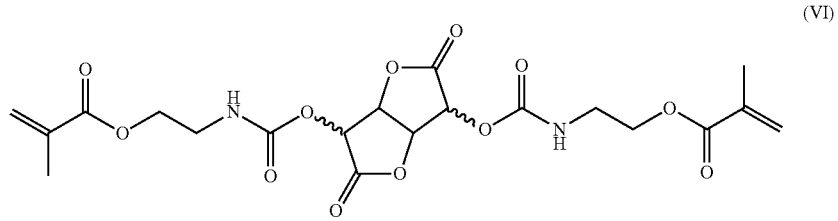 [SMILES: C=C(C)C(=O)OCCNC(=O)OC1C(=O)OC2C(OC(=O)NCCOC(=O)C(=C)C)C(=O)OC12]

where if the chirality is R, R, the compound is glucarodilactone methacrylate (GDMA) and if the chirality is R, S, the compound is mannarodilactone methacrylate (MDMA).

materials development. The presence of both diol and dilactone functionality affords two routes for polymer design from GDL and MDL. As dilactones, they have been used in conjunction with various diamines to produce a class of polymers known as polyhydroxy polyamides via opening of the lactone ring (Hashimoto, K.; Okada, M.; Honjou, N. *Makromol. Chem. Rapid Commun.* 1990, 11, 393-396; Hashimoto, K.; Wibullucksanakul, S.; Matsuura, M.; Okada, M. *J. Polym. Sci. A. Polym. Chem.* 1993, 31, 3141-3149; Kiely, D.; Chen, L.; Lin, T. *J. Am. Chem. Soc.* 1994, 116, 571-578; Liu, Y.; Reineke, T. M. *J. Am. Chem. Soc.* 2005, 127, 3004-3015; and Kiely, D. E.; Chen, L.; Lin, T. *J. Polym. Sci. A. Polym. Chem.* 2000, 38, 594-603, the disclosures of which are incorporated herein by reference thereto to the extent they do not conflict). In contrast to typical aliphatic polyamides that are stable towards hydrolysis, polyhydroxy polyamides have been shown to degrade under mild aqueous conditions (Liu, Y.; Reineke, T. M. *Biomacromolecules.* 2010, 11, 316-325, the disclosure of which is incorporated herein by reference thereto to the extent it does not conflict).

Alternatively, the dilactones could be polymerized through the secondary alcohols. For example, Hashimoto and coworkers synthesized polyurethanes by coupling GDL and MDL with isocyanates in the presence of dibutyltin dioxide (DBTDL) (Wibullucksanakul, S.; Hashimoto, K.; Okada, M. *Macromol. Chem. Phys.* 1997, 198, 305-319; Wibullucksanakul, S.; Hashimoto, K.; Okada, M. *Macromol. Chem. Phys.* 1996, 197, 1865-1876; and Hashimoto, K.; Wibullucksanakul, S.; Okada, M. *J. Polym. Sci. A. Polym. Chem.* 1995, 33, 1495-1503, the disclosures of which are incorporated herein by reference thereto to the extent they do not conflict). To date, these structures have been the only examples that contain the dilactone structure intact within a polymer backbone. In that study, they revealed that although polyurethanes typically resist hydrolysis, the polyurethanes prepared with GDL or MDL degraded readily in phosphate buffered solutions (pH 4-8). They proposed a degradation mechanism consisting of hydrolytic ring opening of the dilactone, followed by scission of the urethane bond (Hashimoto, K.; Wibullucksanakul, S.; Okada, M. *J. Polym. Sci. A. Polym. Chem.* 1995, 33, 1495-1503, the disclosure of which is incorporated herein by reference thereto to the extent it does not conflict).

Dimethacrylate monomers, an example of a possible compound of formula V, are ubiquitous and can be utilized in coatings, structural materials, adhesives, chromatography packing, and biomaterials (i.e. dental composites). Bulk polymerization of dimethacrylates results in highly cross-linked thermoset polymer networks, which yields highly stable structures. The final conversion value is an important parameter for the mechanical properties of poly(dimethacrylates), which also highly depends on the reaction conditions and, particularly, the chemical structure of monomer (Sideridou, I. D.; Achilias, D. S.; Karava, O. *Macromolecules.* 2006, 39, 2072-2080; and Bowman, C. N.; Peppas, N. A. *Macromolecules.* 1991, 24, 1914-1920, the disclosures of which are incorporated herein by reference thereto, to the extent they do not conflict). Renewable monomer sources for these materials and products could offer environmentally benign properties such as degradability and low toxicity, which can further increase applicability. Examples of degradable dimethacrylate chemistries previously utilized include acetals and anhydrides that undergo hydrolysis, and tertiary esters that degrade by thermolysis. Poly(dimethacrylates) from these monomer types have been evaluated for controlled drug release, nanoimprint lithography, and reworkable electronic components (Ogino, K.; Chen, J.-S.; Ober, C. K. *Chem. Mater.* 1998, 10, 3833-3838; Palmieri, F.; Adams, J.; Long, B.; Heath, W.; Tsiartas, P.; Willson, C. G. *ACS Nano* 2007, 1, 307-312; and Anseth, K. S.; Quick, D. J. *Macromol. Rapid. Commun.* 2001, 22, 564-572 the disclosures of which are incorporated herein by reference thereto, to the extent they do not conflict).

Also disclosed are polymers, either homopolymers or copolymers, formed by polymerizing a compound of formula V above. Free radical polymerization of monomers presented herein can provide crosslinked materials. Polymers formed using disclosed monomers can be formed using bulk polymerization, solution casting, or precipitation polymerization and can be formed in bulk articles, films, coatings, microspheres, or microparticles. The polymers can be utilized for coatings, chromatography, microparticles, bio-materials, drug delivery, dental composites, and lithography, for example.

Polymers formed from disclosed monomers may be able to undergo degradation in basic conditions, but remain stable in neutral and acidic environments. Polymers formed from disclosed monomers may be useful in a number of applications, including, for example coatings, chromatography, microparticles, bio-materials, drug delivery, dental composites, and lithography.

In some embodiments, disclosed monomers can be those formed by reacting a compound(s) including a sugar derived compound containing a lactone and two hydroxyls (for example GDL, MDL, or combinations thereof) with a compound(s) containing at least one reactive group. A variety of typical condensation reactions such as esterifications or etherifications can be used to prepare disclosed monomers. In addition the facile reaction between hydroxy containing monomers and isocyantes can be used to generate the corresponding functionalized and reactive monomers. In some embodiments the at least one reactive group can include, for example an isocyanate and an acrylate or methacrylate.

Scheme I below shows an example of an illustrative reaction where a compound(s) of formula III is reacted with a compound(s) of formula IV to result in monomers of formula V.

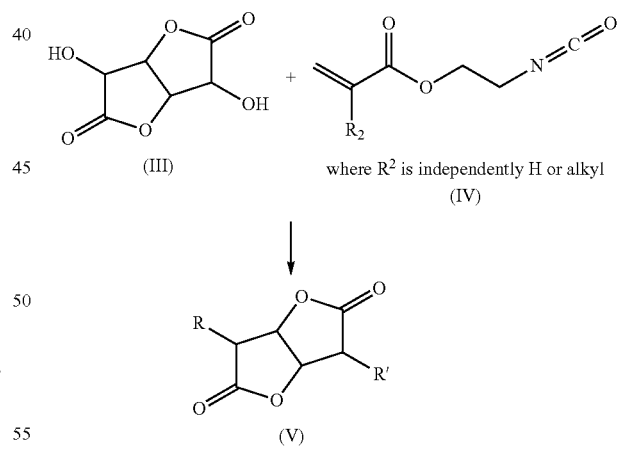

where $R^2$ is independently H or alkyl (IV)

(V)

where R and R' are as defined above with R and R' both selected from

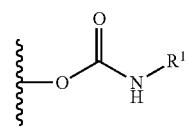

where R¹ is

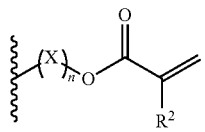

with X independently being a $C_2$ alkyl group, n being 1 and $R^2$ independently being H or a $C_1$ to $C_3$ alkyl.

Scheme I

The compounds of formula III were discussed above, and contain as examples GDL, MDL and mixtures thereof. The compounds of formula IV are generally compounds that contain an isocyanate group and an acrylate or a methacrylate group. Illustrative representatives of compounds of formula IV can include, for example 2-isocyanatoethyl methacrylate (ICM) and 2-isocyanatoethyl acrylate.

Polymers of disclosed monomers are also disclosed herein. Disclosed monomers (e.g., those of formula V and optionally other monomers) can be polymerized using free radical polymerization for example. Any type of free radical polymerization method could be utilized, including for example, thermal initiation, through the use of initiators, or combinations thereof. Illustrative initiators that can be utilized can include, for example peroxides/hydroperoxides, azo compounds, redox initiators, and photoinitiators. In some embodiments, peroxide/hydroperoxide based initiators can be utilized.

Polymers disclosed herein can include homopolymers and copolymers. In some embodiments, homopolymers containing any monomer of formula V, such as GDMA or MDMA for example, can be formed. Disclosed copolymers can include copolymers containing more than one specific type of disclosed monomer of formula V as well as copolymers containing at least one specific type of disclosed monomer of formula V and one or more other monomer not of formula V. In some embodiments, copolymers containing GDMA can be formed. In some embodiments, copolymers containing MDMA can be formed. In some embodiments, copolymers containing both GDMA and MDMA can be formed. In some embodiments, copolymers containing GDMA or MDMA (or both) and a monomer not of formula V can be formed.

In some embodiments, illustrative monomers not of formula V that can be polymerized with a monomer of formula V can include monomers of formula VII below:

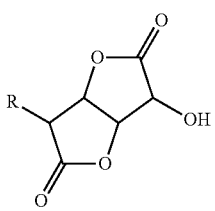

(VII)

where R is selected from the following:

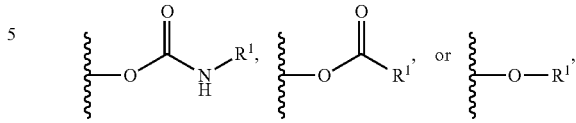

in which R¹ is independently selected from: non-reactive groups or reactive groups. Illustrative reactive groups that can be utilized as R¹ in R can include

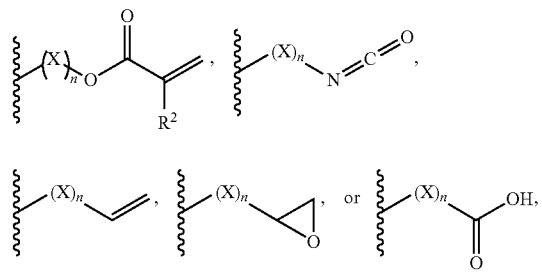

where X is a linking group; n is an integer greater than or equal to one (1) and $R^2$ is hydrogen (H), or an alkyl. Illustrative non-reactive groups can include, for example saturated hydrocarbons, aromatic hydrocarbons, halogenated hydrocarbons, ethers, and esters.

In some embodiments, the monomer not of formula V can include methacrylate or acrylate monomers for example (or both). Other illustrative methacrylate or acrylate monomers can include UDMA, Bis-GMA, ethyleneglycol dimethacrylate, or similar compounds.

Polymers can be formed using any polymerization methods, including for example bulk polymerization, solution casting, precipitation polymerization (for forming microparticles or otherwise), polymerization in solution (for forming branched polymers). Polymers can be formed into bulk articles, films, coatings, microspheres, microparticles for example.

Disclosed polymers can be utilized for virtually any application, including, for example coatings, chromatography, microparticles, bio-materials, drug delivery, dental composites, and lithography, for example.

EXAMPLES

Presented herein as an example of the disclosed monomers, polymers, and articles is the following. GDL and MDL were individually combined with 2-isocyanoehtyl methacrylate (ICM) to form a dimethacrylate feedstock, glucaro-dimethacrylate (GDMA) and mannaro-dimethacrylate (MDMA). GDMA and MDMA were then polymerized. A summary of the entire example can be seen in Scheme II below.

Scheme II

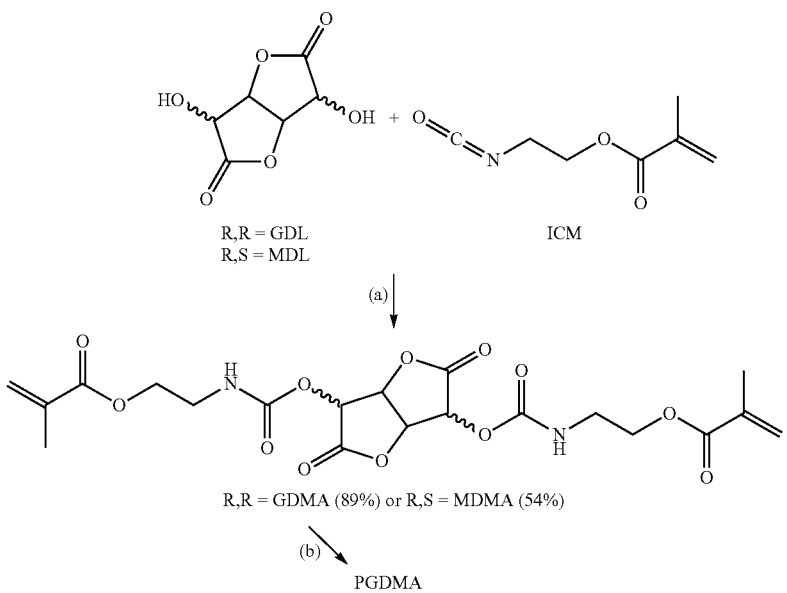

Methods $^1$H-NMR was performed on a Varian VI-500 and $^{13}$C-NMR was performed on a Varian VI-300. FT-IR was performed on a Nicolet Magna-IR 750 spectrometer. ATR FT-IR was performed using a Bruker Alpha Platinum ATR spectrometer. High resolution mass spec was performed using a Bruker Bio-TOF II in positive mode ESI. A Perkin Elmer Pyris Diamond TG/DTA 6300 at a heating rate of 10° C./min was used for TGA. DSC measurements were carried out using a TA Instruments Discovery DSC under $N_2$. Tensile testing was performed using a Minimat Tensile Tester on samples with a dog bone geometry. SEM samples were coated with ~10 nm gold-palladium using a Denton DV-502A high vacuum deposition system and imaging was performed on a Hitachi S-900. DLS was performed using a Malvern Instrument Zetasizer Nano ZA. Contact angle measurements were performed by imaging a drop of DI $H_2O$ applied to a surface and measuring the contact angle using Adobe Photoshop.

Materials

Unless otherwise noted, all chemicals were purchased from Aldrich, Inc. and used without further purification. 2-isocyanatoethyl methacrylate (ICM) was purchased from TCI and used as received.

Synthesis of GDL and MDL

GDL was synthesized according to the literature (Gehret, T. C.; Frobese, A. S.; Zerbe, J. S.; Chenault, H. K. J. Org. Chem. 2009, 74, 8373-8376, the disclosure of which is incorporated herein by reference thereto, to the extent it does not conflict). Briefly, to calcium D-glucarate tetrahydrate (50 g, 0.156 mol) in acetone/water (150 ml, 95/5), $H_2SO_4$ (15.6 g) was added dropwise with stirring. After refluxing for 4 hrs, the reaction was allowed to cool to room temperature. The $CaSO_4$ was filtered off and rinsed 3×50 ml acetone/water (95/5). After adjusting the volume of the filtrate to 310 ml by addition of acetone, 337 ml methyl isobutyl ketone was added. ~310 ml acetone was removed by fractional distillation, followed by refluxing for ½ hr. Fractional distillation was continued to remove a total of 425 ml of solvent. After hot filtration, the product was allowed to crystallize under a stream of $N_2$. The crystallized product was collected by filtration and the mother liquor was concentrated to ~½ volume to collect a second crop of crystallized product. Structure and purity of the product was confirmed by $^1$H-NMR and $^{13}$C-NMR. Yield: 16.8 g, 62%.

MDL was synthesized as previously reported (Liu, Y.; Reineke, T. M. J. Am. Chem. Soc. 2005, 127, the disclosure of which is incorporated herein by reference thereto, to the extent it does not conflict). Briefly, D-mannitol (15 g, 82.4 mmol) in a solution of concentrated $HNO_3$ (42.5 ml) and water (10 ml) was heated at 60° C. with stirring. Upon vigorous evolution of $NO_2$ gas the solution was cooled in an ice bath until the evolution of gas subsided. The reaction was then heated at 60° C. for 4 hrs followed by 85° C. for 30 mins. The solvent was removed under reduced pressure and the product was recrystallized from ethanol. The structure and purity of the product was confirmed by $^1$H-NMR and $^{13}$C-NMR. Yield: 2.58 g, 18%.

The synthesis of GDL proceeded in ~62% yield, produces only benign byproducts, and is easily scalable (Gehret, T. C.; Frobese, A. S.; Zerbe, J. S.; Chenault, H. K. J. Org. Chem. 2009, 74, 8373-8376, the disclosure of which is incorporated herein by reference thereto, to the extent it does not conflict). On the other hand, the synthesis of MDL proceeded in ~18% yield and is accompanied by the evolution of $NO_2$, rendering scale up in a laboratory setting more challenging (Hashimoto, K.; Wibullucksanakul, S.; Matsuura, M.; Okada, M. J. Polym. Sci. A. Polym. Chem. 1993, 31, 3141-3149; Liu, Y.; Reineke, T. M. J. Am. Chem. Soc. 2005, 127, 3004-3015; and Kiely, D. E.; Chen, L.; Lin, T. J. Polym. Sci. A. Polym. Chem. 2000, 38, 594-603, the disclosures of which are incorporated herein by reference thereto, to the extent they do not conflict).

Synthesis of GDMA and MDMA

The monomers glucaro-dimethacrylate and mannaro-dimethacrylate (GDMA and MDMA, respectively) were readily synthesized in two steps from commercially available sources (Scheme 1). The introduction of a methacrylate moiety was achieved using a DBTDL catalyzed alcohol isocyanate coupling reaction between GDL or MDL and isocyanatoethyl methacrylate (ICM).

Specifically, GDMA was synthesized as follows. GDL (4.00 g, 23.0 mmol) was dissolved in dry tetrahydrofuran (THF) (25 ml) in a flame dried flask. ICM (8.61 g, 55.6 mmol) and dibutyltin dilaurate (DBTDL) (27 µl, 46 µmol) were added to the flask. The mixture was stirred at room temperature for 4 hours, after which the precipitate was collected by filtration and thoroughly rinsed with diethyl ether ($Et_2O$) to give GDMA.

The GDMA was a white crystalline powder with a 89% yield. The GDMA was characterized using procedures discussed above. The melting point (m.p.) was determined to be 118° C. The $^1$H-NMR spectra of the GDMA can be seen in FIG. 1. The specifics of the spectra include: $^1$H-NMR (DMSO-$d_6$, 500 MHz): $\delta_{ppm}$: 7.22 (t, J=5.9 Hz, 1H), 7.17 (t, J=5.6 Hz, 1H), 6.10 (d, J=8.8 Hz, 2H), 5.62 (m, 2H), 5.51 (m, 2H), 5.41 (s, 1H), 4.96 (s, 1H), 4.20 (m, 4H), 3.48 (4H, multiplet), 1.90 (6H, s). The $^{13}$C-NMR spectra of the GDMA can be seen in FIG. 2. The specifics of the spectra include: $^{13}$C-NMR (acetone-$d_6$, 90 MHz): $\delta_{ppm}$: 171.46, 171.25, 167.53, 167.50, 156.17, 156.12, 137.20, 126.17, 126.14, 80.48, 75.89, 74.48, 68.74, 64.04, 63.96, 41.06, 40.99, 18.43. The specifics of the FT-IR spectra include: FT-IR (KBr pellet): $\nu_{cm^{-1}}$: 3369 (N—H), 2966 (C—H), 1783 (lactone C=O), 1733 (C=O), 1635 (methacrylate C=C), 1546 (N—H). MS (ESI-TOF, m/z) Calcd. for $C_{20}H_{24}N_2O_{12}$: 484.1329; found: 507.1243 (M+Na$^{30}$); error 4.3 ppm.

Figure 3:
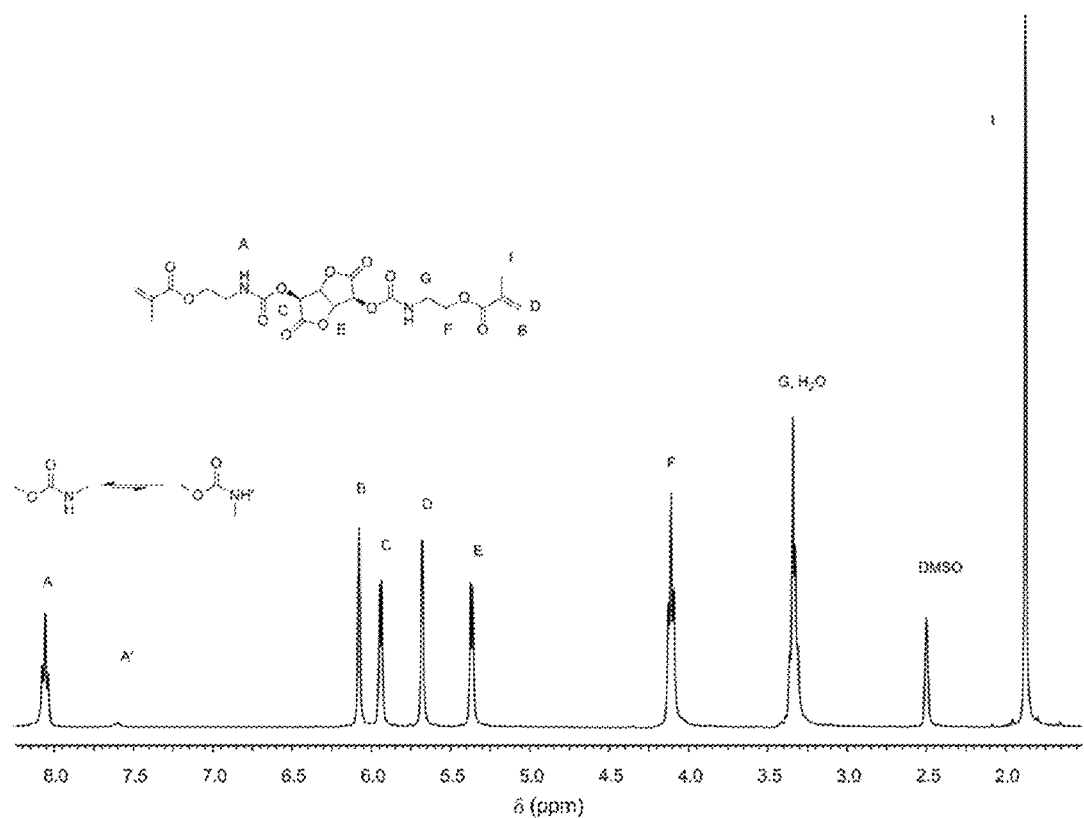
FIG. 3 is a $^1$H-NMR spectrum of MDMA (DMSO-$d_6$, 500 MHz).
Figure 4:
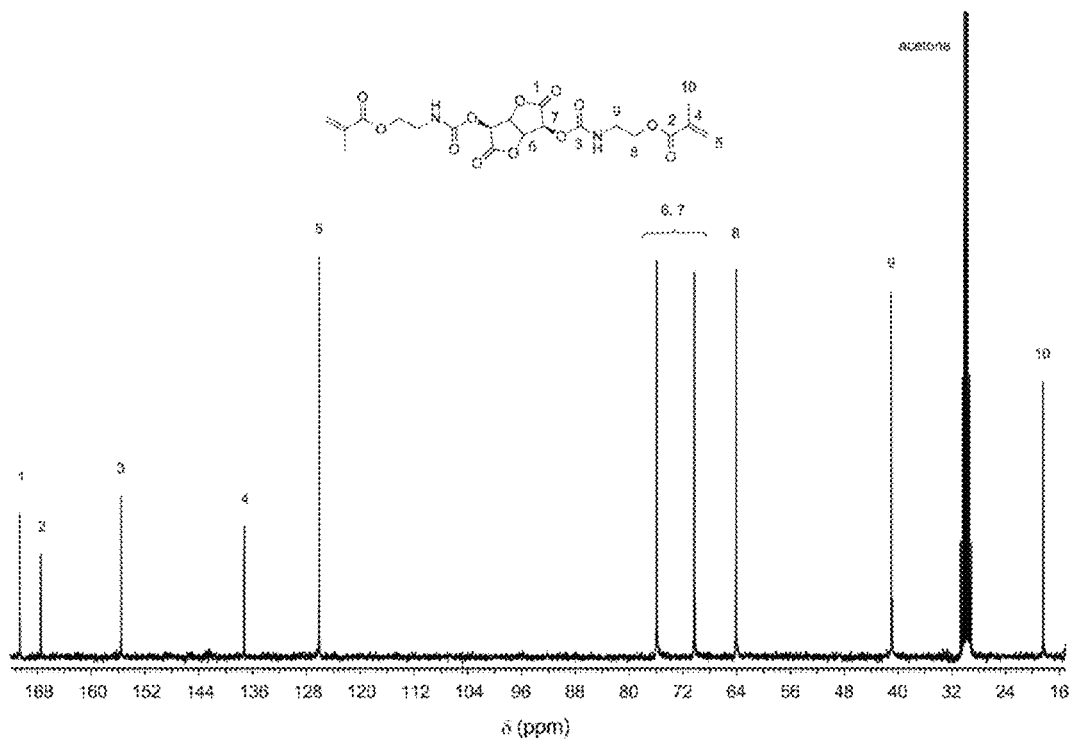
FIG. 4 is a $^{13}$C-NMR spectrum of MDMA (acetone-$d_6$, 90 MHz).

Specifically, MDMA was synthesized as follows. MDL (332 mg, 1.91 mmol) was dissolved in a 50/50 (v/v) mix of dimethylformamide (DMF) and THF (10 ml). ICM (2.0 ml, 14 mmol) and DBTDL (5 µl, 10 µmol) were added and the reaction was left to stir at room temperature for 24 hrs. The solvent was then removed under reduced pressure without heating and the crude product was recrystallized from an ethyl acetate/hexanes solvent pair to give a white crystalline powder. Even with a large excess of ICM and a longer reaction time, the synthesis of MDMA offered only ~54% yield. The MDMA was characterized using procedures discussed above. The $^1$H-NMR spectra of the MDMA can be seen in FIG. 3. $^1$H-NMR (DMSO-$d_6$, 500 MHz): $\delta_{ppm}$: 8.06 (t, J=5.7 Hz, 2H), 6.07 (s, 2H), 5.94 (d, J=6.1 Hz, 2H), 5.68 (s, 2H), 5.37 (d, J=6.1 Hz, 2H), 4.11 (t, J=8.5 Hz, 4H), 3.33 (t, J=8.5 Hz, 4H), 1.88 (s, 6H). The $^{13}$C-NMR spectra of the MDMA can be seen in FIG. 4 $^{13}$C-NMR (acetone-$d_6$, 90 MHz): $\delta_{ppm}$: 170.63, 167.50, 155.54, 137.22, 126.11, 75.89, 70.30, 64.11, 41.02, 18.43. MS (ESI-TOF, m/z) Calcd. for $C_{20}H_{24}N_2O_{12}$: 484.1329; found: 507.1221 (M+Na$^+$); error 1.2 ppm.

The difference in yields between GDMA and MDMA are thought to be due to the puckered conformations of the dilactone structures. The dilactone structures adopt puckered conformation and as a result, hydroxyl groups in the endo position are located above the lactone ring. MDL has both hydroxyls in endo positions, while GDL has one hydroxyl in the endo position and one in the exo position. When one of the hydroxyls of MDL is functionalized with a rather bulky carbamate ethylene methacrylate group, the steric crowding on the endo face of the dilactone ring is exacerbated and the other hydroxyl group is therefore much harder to functionalize. By contrast, the hydroxyls of GDL are on opposite sides of the dilactone ring and thus their respective steric environments are independent of each other.

Bulk Polymerization of GDMA

Figure 5:
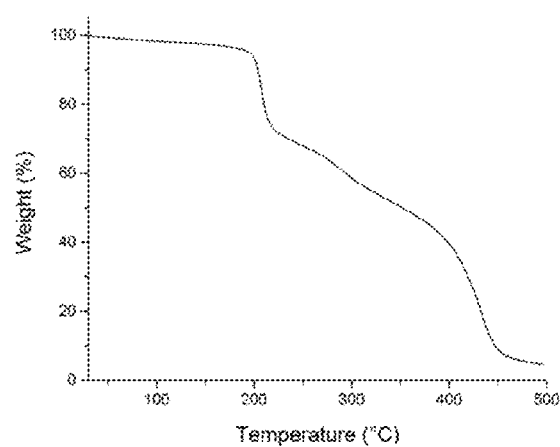
FIG. 5 is TGA data for GDMA (heating rate=10° C./min).

GDMA was selected for initial studies of polymers from dimethacrylates with a dilactone core. Polymerization in the bulk required a temperature that was between the melting point (m.p.) and the onset of decomposition ($T_d$) of GDMA. The m.p. of GDMA was determined to be 118° C. and TGA revealed that the $T_d$ was 166° C. (See FIG. 5). Thus, a temperature of 135° C. was selected for the bulk polymerization of GDMA. Using 1.5 wt % of the radical initiator, dicumyl peroxide (DCP), PGDMA samples were formed by compression molding in a stainless steel tensile bar mold with Teflon inserts. Curing at 135° C. for 30 minutes afforded PGDMA as opaque, off yellow samples.

Specifically, the bulk polymerization was undertaken as follows. GDMA and dicumyl peroxide (DCP) (1.5 wt %) were dissolved in $CH_2Cl_2$ with stirring and the solvent was removed by rotary evaporation. The resulting powder (approx. 90 mg) was loaded into the stainless steel tensile bar mold between two Teflon inserts and heated in an oven at 135° C. After 30 minutes, the sample was removed from the mold and allowed to cool. FT-IR (KBr pellet) showed: $\nu_{cm^{-1}}$: 3376 (N—H), 2969 (C—H), 1805 (lactone C=O), 1735 (C=O), 1635 (C=C), 1537 (N—H).

Figure 6:
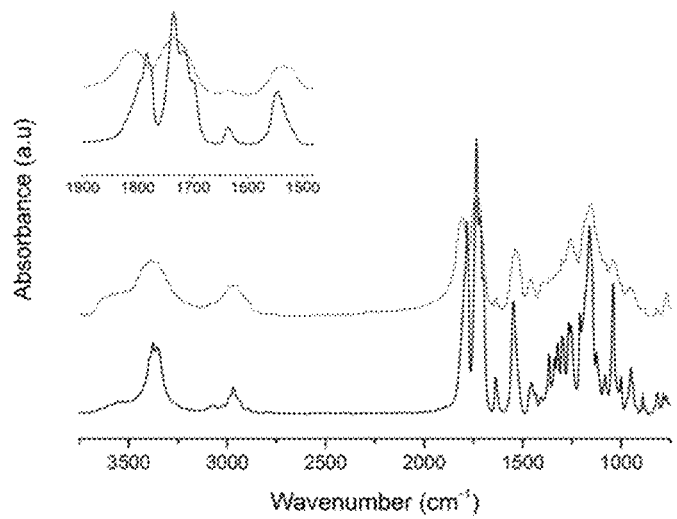
FIG. 6 are FT-IR spectra of GDMA (-) and PGDMA (······) Inset is region used for determining fractional conversion of methacrylate groups.

The fractional conversion (p) of methacrylate groups was determined by FT-IR (See FIG. 6). Quantifying the conversion of methacrylate groups by this technique required standardizing the area under the absorbance peak corresponding to the methacrylate C=C stretch (1635 cm$^{-1}$) between the GDMA and PGDMA spectra relative to an internal standard. For poly(dimethacrylates), an IR-active functional group unaffected during polymerization serves as the internal standard (Sideridou, I.; Tserki, V.; Papanastasiou, G. Biomaterials. 2002, 23, 1819-1829, the disclosure of which is incorporated herein by reference thereto, to the extent it does not conflict). In this particular case, the carbonyl stretch and N—H bend were used as internal standards. The values of p obtained using each internal standard were in good agreement with each other, with an average value of p=0.64. The inability to obtain full conversion was due to unreacted methacrylate groups becoming physically entrapped as the reaction mixture underwent vitrification during polymerization. The gel fraction of PGDMA was determined to be 97.8 wt % by soxhlet extraction with $CH_2Cl_2$.

The masses of PGDMA before and after extraction, along with the value of p determined by FT-IR (FIG. 6), were used to calculate values for crosslink density (i.e., the mole fraction of repeat units that are crosslinks, a) and molar mass between crosslinks ($\overline{M_c}$) of 0.46 and 1.1 kg/mol, respectively (Eqs. 1 and 2). Three parallel samples of PGDMA were weighed ($m_1$) and subjected to soxhlet extraction by $CH_2Cl_2$ for 24 hours. The samples were then dried in a vacuum oven overnight at 50° C. and weighed ($m_2$). The crosslink density (a) and network parameter ($M_c$) were calculated according to equations 1 and 2, where p is the fractional conversion determined by FT-IR and $M_0$ is the molecular weight of GDMA.

$$a = \frac{2pm_1 - m_2}{pm_1} \qquad \text{Eq. 1}$$

$$M_c = M_0/a \qquad \text{Eq. 2}$$

Figure 2:
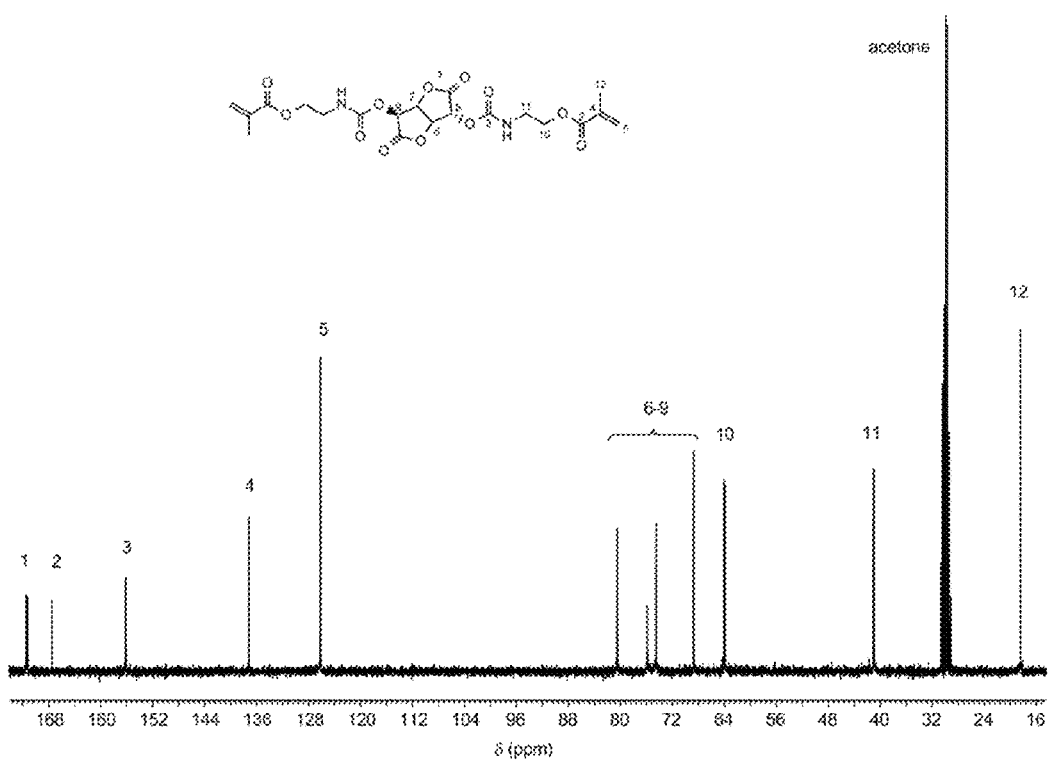
FIG. 2 is a $^{13}$C-NMR spectrum of GDMA (acetone-$d_6$, 90 MHz).

The values of p, a, and $\overline{M_c}$ for PGDMA are comparable to those previously reported for commercially available dimethacrylate thermosets (example reported values for P(UDMA) as shown in FIG. 2: p=0.70; a=0.57; ($\overline{M_c}$)=822 g/mol) (Sideridou, I.; Tserki, V.; Papanastasiou, G. Biomaterials. 2002, 23, 1819-1829; Sideridou, I.; Tserki, V.; Papanastasiou, G. *Biomaterials*. 2003, 24, 655-665; and Barszczewska-Rybarek, I.; Gibas, M.; Kurcok, M. *Polymer*. 2000, 41, 3129-3135, the disclosures of which are incorporated herein by reference thereto, to the extent they do not conflict).

Figure 7:
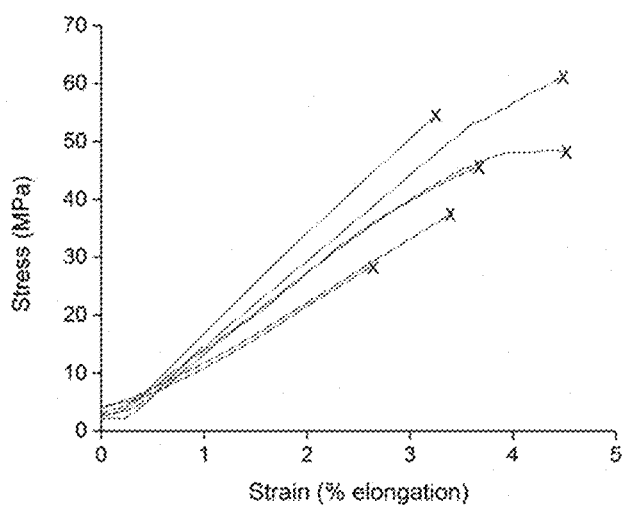
FIG. 7 shows tensile testing for various samples of PGDMA. X denotes break point and defines both the ultimate elongation and ultimate tensile strength.

Tensile testing was performed to investigate the mechanical properties of the PGDMA. Results of this testing are shown in FIG. 7. Values for Young's modulus, ultimate tensile stress, and elongation at break were 1.4±0.2 GPa, 51±13 MPa, and 3.7±0.7%, respectively. The low elongation at break and high modulus, indicative of a stiff and brittle material, are a result of the densely crosslinked network. The modulus of PGDMA is comparable to previously reported values for the moduli of thermosets from the related, rigid, and commercially available bisphenol A glycidyl methacrylate (bis-GMA) and urethane dimethacrylate (UDMA) monomers, whose structures are shown below as formula (VIII) and (IX).

Figure 8:
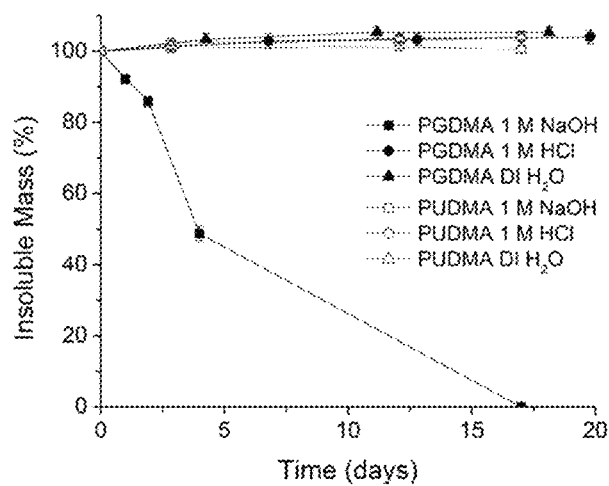
FIG. 8 shows the stability of PGDMA and PUDMA in aqueous media.

Results of this testing can be seen in FIG. 8. In 1 M NaOH, PGDMA samples readily degraded and became completely water soluble after 17 days. By contrast, PGDMA was stable in both DI $H_2O$ and 1 M HCl. The loss of mass in basic conditions indicated that the crosslinked network eroded to yield water soluble degradation products. In acidic and neutral conditions the final mass of PGDMA was over 100% due to swelling of the polymer network. To demonstrate the role of the dilactone in the degradation of PGDMA, the stability of poly(UDMA) was also evaluated in the same environments. The commercially available monomer UDMA served as a structural analogue to GDMA without a dilactone core. The stability of poly(UDMA) at all conditions examined indicated the key role of the dilactone moiety in the degradation of PGDMA (and not the urethane linkage).

To investigate the degradation products, PGDMA was degraded in 1 M $NaOD/D_2O$ and analyzed by $^1H$-NMR spectroscopy. Spectra from this analysis can be seen in

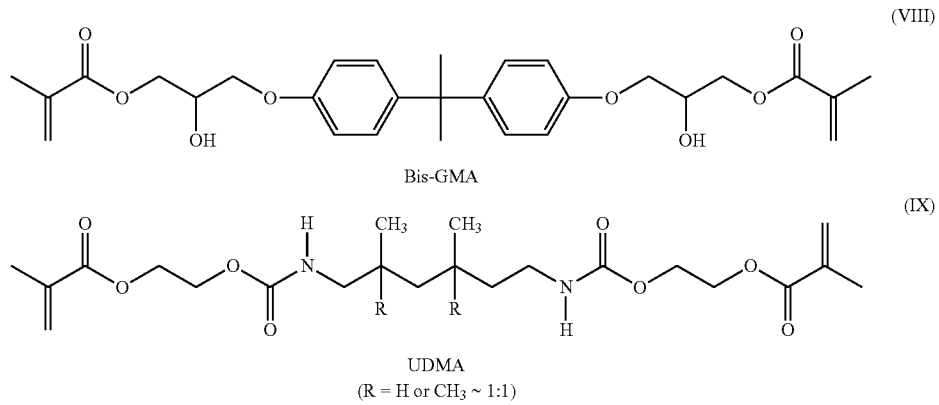

Moduli for the related P(bis-GMA) and P(UDMA) as shown above are also ~1.4 GPa (Sideridou, I.; Tserki, V.; Papanastasiou, G. *Biomaterials*. 2003, 24, 655-665, the disclosure of which is incorporated herein by reference thereto, to the extent it does not conflict). GMDA falls into the stiff dimethacrylate category and this can be attributed to the fused dilactone ring structure, as well as hydrogen bonding between the urethane groups.

Degradation of Bulk Polymerized PGDMA

The stability of bulk polymerized PGDMA in aqueous environments was evaluated by submerging samples in neutral, acidic, and basic solutions and monitoring the mass of insoluble polymer over time. Specifically, the stability of PGDMA in deionized (DI) $H_2O$ and 1M HCl and poly urethane dimethacrylate (PUDMA) in 1M NaOH was evaluated as follows: three parallel samples of each polymer (~50 mg) were immersed in the appropriate aqueous solution (10 ml) and allowed to sit undisturbed at room temperature. The samples were periodically removed, blotted dry, weighed, and reimmersed in the same solution. For the stability of PGDMA in 1M NaOH, three parallel samples of PGDMA (~50 mg) for each time point were immersed in solution (10 ml) and allowed to sit undisturbed at room temperature. At each time point the insoluble mass was collected by filtration, dried in a vacuum oven at 50° C. overnight and weighed. Degraded samples for NMR analysis were prepared by immersing PGDMA in a 1 M heavy sodium hydroxide (NaOD) in deuterium oxide ($D_2O$) solution until the mixture became homogeneous.

FIGS. 9A and 9B Analysis of the crude degradation mixture showed the presence of 2-aminoethanol and methacrylic acid, as well as broad resonances corresponding to the methacrylic polymer backbone (FIG. 9A). The integration area of vinyl protons from unreacted methacrylate groups compared to that of resonances corresponding to the polymer backbone gave an apparent p=0.78. This value is higher than what was determined by FT-IR, possibly due to the remaining methacrylate groups undergoing reaction during the degradation process. The resonances between 3.7 and 4.0 ppm are likely due to products from the degradation of the dilactone units, however the lack of resolution prevented any specific structural assignment.

$^1H$-NMR data for the high molar mass component of degraded PGDMA isolated by dialysis indicates the presence of poly(2-aminoethyl methacrylate) (PAMA) and poly (2-hydroxyethyl methacrylamide) (PHEMa) repeat units (FIG. 9B). A substoichiometric ratio of PAMA and PHEMa side chain resonances to that of the polymer backbone suggests partial hydrolysis of the methacrylate ester to a poly(methacrylic acid) (PMAA) repeat unit. Comparison of the areas for the aromatic protons of the DCP initiator fragment and the polymer backbone gives a number average degree of polymerization ($N_n$)=49. Based on these data, a proposed degradation pathway of PGDMA is outlined in Scheme III below.

Scheme III. Degradation pathways of PGDMA

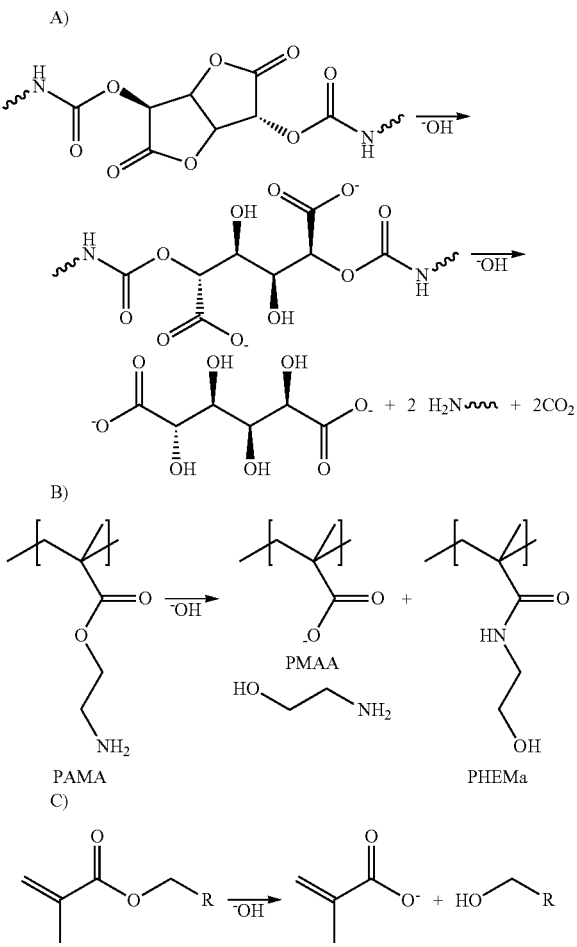

A) ring-opening of the dilactone followed by urethane scission,
B) degradation of poly(aminoethyl methacrylate) via hydrolysis and intermolecular amidation,
C) hydrolysis of unreacted methacrylate groups.

The degradation of the dilactone core likely proceeds by ring opening followed by scission of the urethane bond (Scheme IIIA) analogous to that suggested by Hasimoto and co-workers (Hashimoto, K.; Wibullucksanakul, S.; Okada, M. *J. Polym. Sci. A. Polym. Chem.* 1995, 33, 1495-1503, the disclosure of which is incorporated herein by reference thereto, to the extent it does not conflict). As shown, the polymer structure afforded by removal of the dilactone and urethane units is PAMA. This polymer is known to degrade in basic conditions to give a combination of PHEMa, PMAA, and unaffected PAMA repeat units, as well as elimination of the small molecule 2-aminoethanol (Scheme IIIB) (Thompson, K. L.; Read, E. S.; Armes, S. P. *Polym. Degrad. Stab.* 2008, 93, 1460-1466, the disclosure of which is incorporated herein by reference thereto, to the extent it does not conflict). The presence of methacrylic acid in the crude degradation media is due to simple hydrolysis of unreacted methacrylate groups (Scheme IIIC).

Formation of Polymer Films

PGDMA and P(GDMA-co-MDMA) Films. Given the selective degradability of PGDMA, this material was investigated further for potential film and microsphere applications. PGMDA films can be selectively degraded in base but remain stable in acidic and neutral conditions. Coatings that can be selectively removed under specific conditions are useful in applications such as lithography and drug delivery (Palmieri, F.; Adams, J.; Long, B.; Heath, W.; Tsiartas, P.; Willson, C. G. *ACS Nano* 2007, 1, 307-312; and Kim, B.; Park, S.; Hammond, P. *Acs Nano* 2008, 2, 386-392, the disclosures of which are incorporated herein by reference thereto, to the extent they do not conflict). Aside from using renewable feedstocks, a degradable film is appealing from a sustainability viewpoint since recycling films from consumer waste is a difficult and expensive process.

PGDMA films were initially attempted to be made by casting a solution of GDMA and DCP on to a substrate, followed by removal of the solvent and subsequent thermal curing. Conditions similar to those used for forming the bulk PGDMA material were chosen for film curing (135° C., 20 minutes). A film made using this procedure can be seen in FIG. 10.

This approach allowed films to be made, but did include disadvantages. For one, GDMA has poor solubility in most volatile organic solvents. Although it has good solubility in DMF and DMSO, the high boiling point of these solvents precluded their use. After screening a number of potential candidates, THF was the only suitable solvent that had a low boiling point and was capable of keeping GDMA in an amorphous state during the solvent removal stage. Also, PGDMA films exhibited slight yellowing when formed under the selected conditions (similar to the yellowing observed in the bulk PGDMA samples above). This was likely due to partial thermal decomposition of GDMA. Although the curing temperature of the PGDMA films was below the $T_d$ of GDMA determined by TGA, it is possible that GDMA undergoes a decomposition process at elevated temperatures that is not accompanied by a loss of mass. GDL was previously reported to undergo thermal elimination in the melt at 130° C. to give the acids L-threo- and L-erythro-4-deoxyhex-4-enaro-6,3-lactone (Gehret, T. C.; Frobese, A. S.; Zerbe, J. S.; Chenault, H. K. *J. Org. Chem.* 2009, 74, 8373-8376, the disclosure of which is incorporated herein by reference thereto, to the extent it does not conflict).

Figure 11:
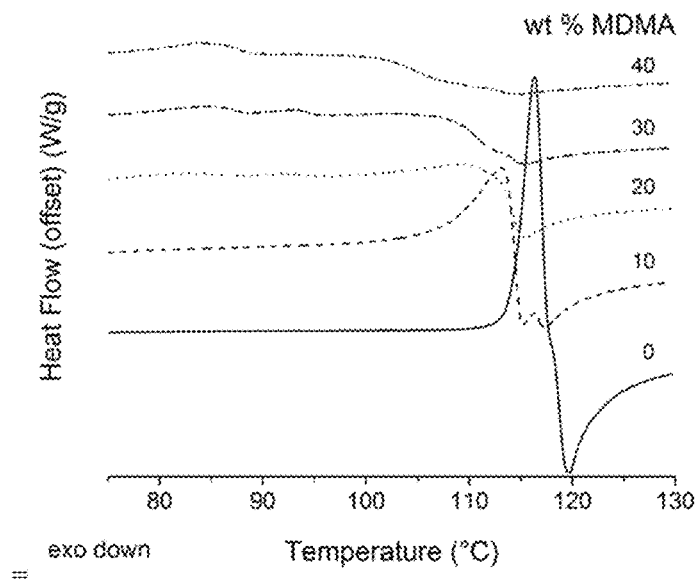
FIG. 11 shows DSC traces of GDMA/MDMA mixtures (ΔT/t=10° C./min).

Furthermore, PGDMA film quality was variable and they often exhibited heterogeneities. This was likely due to the autopolymerization of GDMA upon melting. Differential scanning calorimetry (DSC) of GDMA without initiator revealed a melting endotherm, followed immediately by an exotherm corresponding to polymerization (FIG. 11). Simultaneous melting and polymerization could give rise to a heterogeneous film if unmelted fractions become entrapped by a cured polymer matrix.

The use of a reactive diluent was thought to be able to address the issues noted above by suppressing the crystallinity of the reaction mix and lowering the curing temperature. To this end, a mixture of GDMA and MDMA monomers were used for film generation. DSC traces of GDMA/MDMA mixtures showed a dramatic suppression in both the melting point and the crystallinity with increasing MDMA content (FIG. 11). At 40 wt % MDMA, the crystallinity of the mixture was almost completely suppressed and the melting point was lowered to 85° C. Furthermore, there is baseline separation between the melting point of the mixture and the onset of autopolymerization. This indicated that a mixture of GDMA/MDMA in a 3:2 ratio could be used to make more homogeneous and clear films than those created by the homopolymerization of GDMA.

Therefore, a 3:2 mixture of GDMA/MDMA was utilized to form a polymer film. Specifically, polymer films of GDMA and MDMA were fabricated using a 3:2 mixture of GDMA:MDMA and benzoyl peroxide (BPO) (1.5 wt %).

The mixture was dissolved in acetone (0.10 g/ml). The solution was then applied dropwise to a glass slide and the solvent was removed under reduced pressure. The film was then cured in an oven under ambient atmosphere and pressure at 95° C. for 20 min to give clear homogenous films. ATR-IR (neat): $v_{cm^{-1}}$: 3347 (N—H), 2956 (C—H), 1796 (lactone C=O), 1713 (C=O), 1635 (C=C), 1527 (N—H).

A temperature of 95° C. was selected for curing P(GDMA-co-MDMA) (3:2) films in order to ensure complete melting of the film while avoiding the onset of autopolymerization. The low crystallinity of the co-monomer mixture allowed for a wider range of appropriate casting solvents, with acetone and THF being suitable. Due to the lower curing temperature, BPO was found to be an appropriate substitute for DCP. Curing of the co-monomer films with 1.5 wt % BPO cast from acetone at 95° C. for 15 minutes gave clear homogeneous coatings without any noticeable yellowing.

Figure 12:
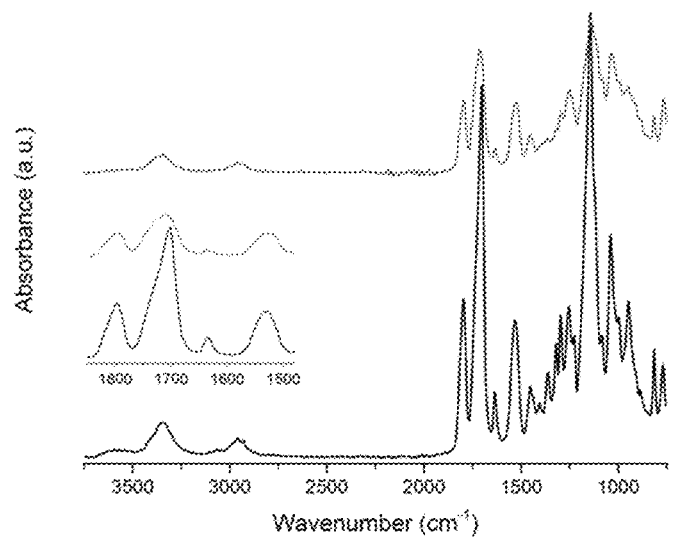
FIG. 12 are ATR-IR spectra of P(GDMA-co-MDMA) films before (-) and after (······) curing. Inset is region used for determining fractional conversion of methacrylate groups.

ATR-IR was used to determine p for the co-polymer films, employing the same process as used above for bulk PGDMA. The results are seen in FIG. 12. Again, the values obtained using either the N—H bend or carbonyl stretch as internal standards were in good agreement, with an average value of p=0.50. Although 50% conversion is within the typical range for poly(dimethacrylates), this conversion value is noticeably lower than that observed for pure PGDMA samples.

Figure 13:
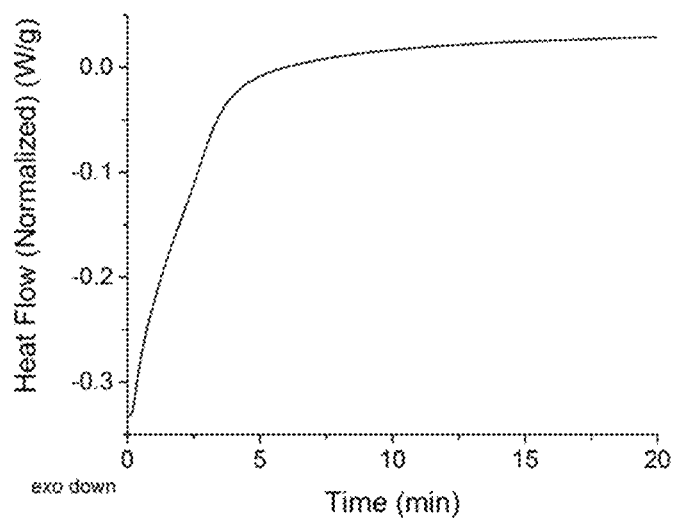
FIG. 13 is an isothermal DSC trace of GDMA:MDMA (3:2) mixture with 1.5 wt % BPO at 95° C.
Figure 14:
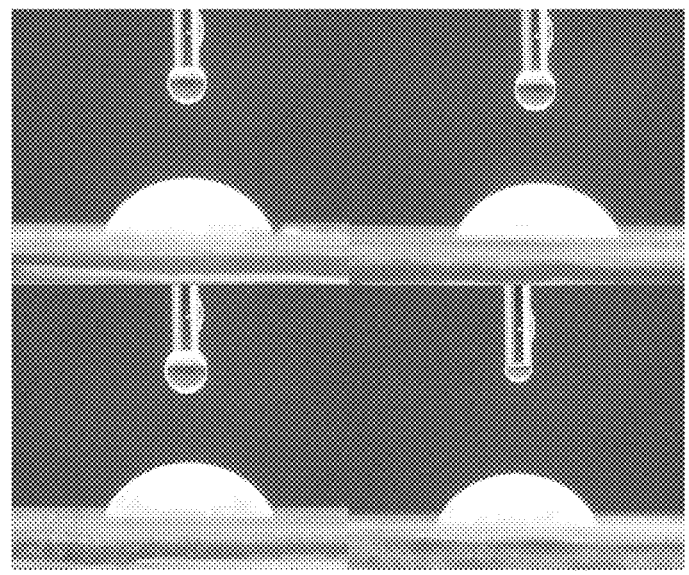
FIG. 14 show images of samples of P(GDMA-co-MDMA) films for contact angle measurements. Each image is of a different sample.

DSC modeling of the curing reaction indicated that this lower conversion value was not due to incomplete reaction time, as the exotherm of polymerization ends after approximately 8 minutes (FIG. 13). The difference in p may be at least partially due to the different reaction temperatures and radical initiators used to form PGDMA and the P(GDMA-co-MDMA) (3:2) films. Additionally, it has been shown that monomer composition can have a significant effect on the value of p obtained for poly(dimethacrylates) (Sideridou, I.; Tserki, V.; Papanastasiou, G. *Biomaterials*. 2003, 24, 655-665, the disclosure of which is incorporated herein by reference thereto, to the extent it does not conflict). Contact angle measurements indicated that the P(GDMA-co-MDMA) (3:2) films were moderately hydrophilic with θ=78.4±0.6° (FIG. 14).

Degradability of Co-Polymer Films

Figure 15:
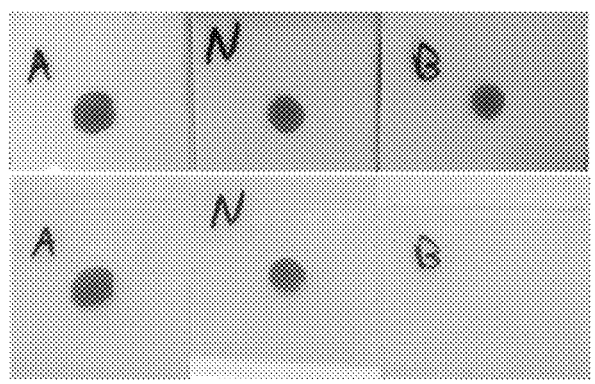
FIG. 15 show images of P(GDMA-co-MDMA) films with Sudan III dye before (top) and after (bottom) being immersed in an aqueous solution for 14 hours. A=1 M HCl, N=DI H$_2$O, and B=1 M NaOH.

The degradability of the co-polymer films was evaluated in a similar manner to the bulk PGDMA above. After being cast onto a glass slide and cured, the samples were immersed in 1 M HCl, DI H$_2$O, or 1 M NaOH solutions for 14 hours. The glass slides were then removed and evaluated. The co-polymer films were clear, thus, a red dye (Sudan III) was added to the solvent casting solution to aid in visual inspection of the films. After 14 hours, the samples immersed in 1 M HCl and DI H$_2$O remained adhered to the glass slide, while the sample immersed in 1 M NaOH completely degraded (FIG. 15). Thus, the stability of the P(GDMA-co-MDMA) (3:2) films in aqueous environments was similar to that of bulk PGDMA.

Formation of PGDMA Microspheres

Polymer microparticles have a wide range of applications, including coatings, drug and gene delivery, biosensors, tissue engineering, nano-reactors, separations, waste water treatment, and enhanced oil recovery. Degradable microparticles are of particular interest in the area of drug and gene delivery, whereby a therapeutic payload is released upon the removal of a polymeric carrier (Li, G. L.; Mohwald, H.; Shchukin, D. G. *Chem. Soc. Rev.* 2013, 42, 3628-3646; and Elsabahy, M.; Wooley, K. *Chem. Soc. Rev.* 2012, 41, 2545-2561, the disclosures of which are incorporated herein by reference thereto, to the extent they do not conflict). They can also be useful as sacrificial templates for synthesis of more complex architectures (e.g., using a degradable core en route to a hollow microsphere) (Li, G. L.; Möhwald, H.; Shchukin, D. G. *Chem. Soc. Rev.* 2013, 42, 3628-3646; and Fu, G.-D.; Li, G. L.; Neoh, K. G.; Kang, E. T. *Prog. Polym. Sci.* 2011, 36, 127-167, the disclosures of which are incorporated herein by reference thereto, to the extent they do not conflict). Fabrication techniques for polymer microspheres include dispersion polymerization, emulsion polymerization, suspension polymerization and precipitation polymerization. The latter can be an appealing option because it can afford clean, uniform polymer microspheres without the use of additives. Precipitation polymerization has been employed to fabricate a variety of microspheres with rather complex architectures (Li, G. L.; Möhwald, H.; Shchukin, D. G. *Chem. Soc. Rev.* 2013, 42, 3628-3646; Li, W.; Stöver, H. *J. Polym. Sci. A. Polym. Chem.* 1998, 36, 1543-1551; Li, W.; Stöver, H. *Macromolecules*. 2000, 33, 4354-4360; and Li, G.; Yang, X. *J. Phys. Chem. B*. 2007, 111, 12781-12786, the disclosures of which are incorporated herein by reference thereto, to the extent they do not conflict).

A typical formulation for a precipitation polymerization consists of a monofunctional monomer, a difunctional crosslinking monomer, radical initiator, and solvent (Li, G. L.; Möhwald, H.; Shchukin, D. G. *Chem. Soc. Rev.* 2013, 42, 3628-3646, the disclosure of which is incorporated herein by reference thereto, to the extent it does not conflict). For thermally initiated precipitation polymerizations, particle formation can be initiated by the aggregation of oligomers that form particles, which, due to the presence of difunctional monomer, have reactive vinyl groups. Subsequent particle growth can occur via the coupling of soluble radical oligomers onto the reactive surface of the growing polymer particle (Downey, J.; Frank, R.; Li, W.; Stöver, H. *Macromolecules*. 1999, 32, 2838-2844, the disclosure of which is incorporated herein by reference thereto, to the extent it does not conflict). Since there are no ancillary components in the reaction medium during a precipitation polymerization, a variety of components affecting the solution conditions of the reaction medium must be carefully controlled, such as the ratio of monofunctional monomer to crosslinking agent, solvent composition, and monomer concentration. Polymer microspheres formed by this method are typically co-polymers, since precipitation polymerizations using only crosslinking monomer tend to give coagulum or irregular microparticles (Saraçoğlu, B.; Uğuzdoğan, E.; Gölgelioğlu, C.; Tuncel, A. *Ind. Eng. Chem. Res.* 2009, 48, 4844-4851; Li, W.; Stöver, H. *J. Polym. Sci. A. Polym. Chem.* 1999, 37, 2899-2907; and Jiang, J.; Zhang, Y.; Guo, X.; Zhang, H. *Macromolecules*. 2011, 44, 5893-5904, the disclosures of which are incorporated herein by reference thereto, to the extent they do not conflict).

Although a wide range of monofunctional monomers have been used in precipitation polymerization, only very few difunctional crosslinking agents have been employed, namely divinyl benzene and ethylene glycol dimethacrylate (Li, G. L.; Möhwald, H.; Shchukin, D. G. *Chem. Soc. Rev.* 2013, 42, 3628-3646, the disclosure of which is incorporated herein by reference thereto, to the extent it does not conflict). To the best of our knowledge, no precipitation polymerization has been performed using a degradable crosslinking monomer. To this end, polymer microspheres were fabricated by precipitation polymerization using GDMA as the crosslinker.

GDMA (10 mg) and azobisisobutyronitrile (AIBN) (0.1 mg) were dissolved in dry THF (1 ml) in a 2 dram screw cap vial. The vial was then placed in thermostated sand bath at 70° C. and allowed to sit without stirring for an allotted amount of time. The milky white suspension was diluted with THF (5 ml), centrifuged (1 min @6500 rpm), and the supernatant was removed by decanting. Two more iterations of the dilution/centrifuge/decanting process were performed to remove any soluble impurities. ATR-IR (thin film THF): $v_{cm^{-1}}$: 3349 (N—H), 2949 (C—H), 1797 (lactone C=O), 1724 (C=O), 1630 (C=C), 1531 (N—H).

For this initial study, methyl methacrylate (MMA) was selected as the monofunctional co-monomer. THF was determined to be the best option due to its ability to solvate the monomers and avoid coagulation during the reaction. The reaction formulations are summarized in Table 1.

TABLE 1

Formulations and characterization of P (GDMA-co-MMA) microspheres formed by precipitation polymerization.

| Entry | Polym. time (h) | GDMA/MMA/ AIBN mol ratio | [GDMA] (mM) | $D_h$[1] (nm) | $D_n$[2] (nm) | PDI[1] | CV[2] (%) |
|---|---|---|---|---|---|---|---|
| 1 | 2 | 100/0/1.48 | 103 | 699 | — | 0.13 | — |
| 2 | 2 | 100/10/1.48 | 103 | 743 | — | 0.13 | — |
| 3 | 2 | 100/20/1.48 | 103 | 832 | — | 0.16 | — |
| 4 | 2 | 100/30/1.48 | 103 | 896 | — | 0.17 | — |
| 5 | 2 | 100/40/1.48 | 103 | 813 | — | 0.11 | — |
| 6[3] | 8 | 100/30/1.48 | 82.6 | — | — | — | — |
| 7 | 8 | 100/30/1.48 | 62.0 | 833 | — | 0.15 | — |
| 8 | 8 | 100/30/1.48 | 41.3 | 738 | 475 | 0.12 | 16 |
| 9 | 8 | 100/30/1.48 | 20.7 | 730 | 428 | 0.12 | 14 |

[1] Determined by DLS.
[2] Coefficient of Variation, determined by SEM.
[3] Coagulated by 8 h.

Figure 16:
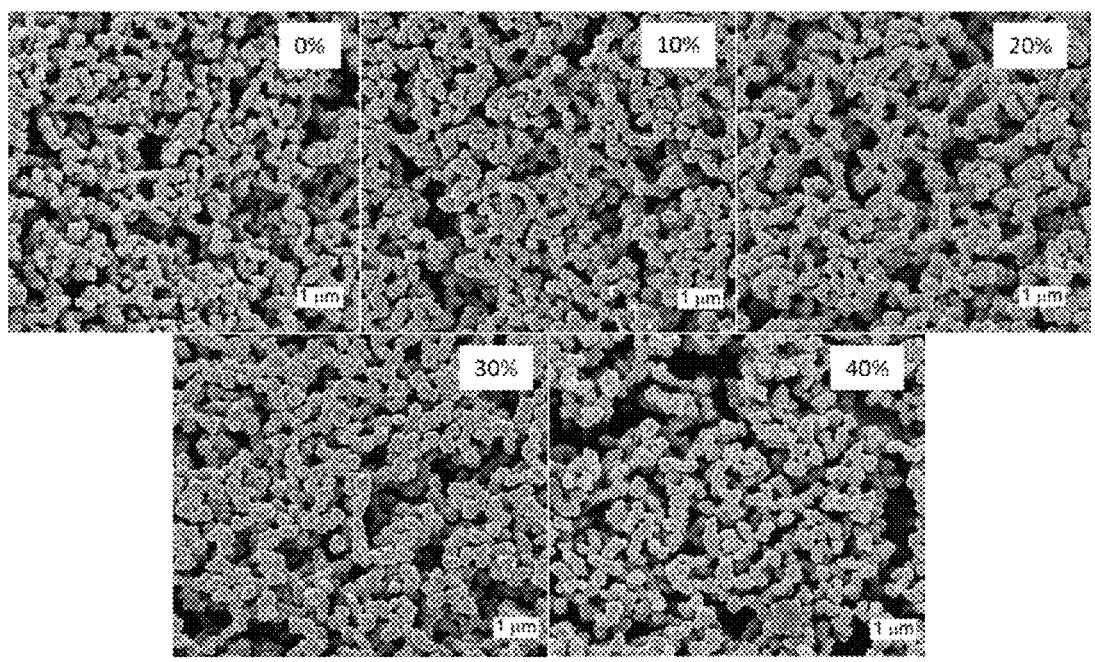
FIG. 16 are SEM images of P(GDMA-co-MMA) microparticles with varying mol % MMA (entries 1-5, Table 1).

All studies were performed at 70° C. without stirring in screw capped vials using AIBN as a source of free-radicals. Initial trials (entries 1-5) maintained a constant concentration of GDMA while varying the ratio of GDMA:MMA. Reaction times greater than 3 hours under these conditions lead to coagulation, so the reaction time was limited to 2 hours. The microparticles were isolated as suspensions in THF after repeated cycles of centrifugation, decanting off the supernatant, and suspension in THF. Dynamic light scattering (DLS) results in THF show an increase in hydrodynamic diameter ($D_h$) with increasing MMA concentration up to 30 mol %. This trend reverses between MMA loadings of 30 and 40 mol % (trials 4 and 5), while MMA loadings of 50 mol % or greater lead to coagulum. A similar trend was previously reported for precipitation polymerizations using divinyl benzene and various monofunctional methacrylates. The polydispersity index (PDI) values between 0.11 and 0.17 for trials 1-5 suggests that the particles were of relatively low dispersity. However, the irregular morphologies of these particles as determined by SEM prevented accurate size determination via imaging (FIG. 16).

The irregular morphologies may have been due to the short reaction time, since longer reaction times typically give more spherically shaped particles for precipitation polymerizations (Li, G. L.; Möhwald, H.; Shchukin, D. G. Chem. Soc. Rev. 2013, 42, 3628-3646, the disclosure of which is incorporated herein by reference thereto, to the extent it does not conflict). However, longer reaction times lead to particle coagulation at [GDMA]=103 mM. This issue was addressed by both lowering the concentration of monomers in solution and extending the reaction time (8 hours), while maintaining a constant ratio of GDMA:MMA of 10:3 (trials 6-9).

Figures 17A, 17B, 17C:
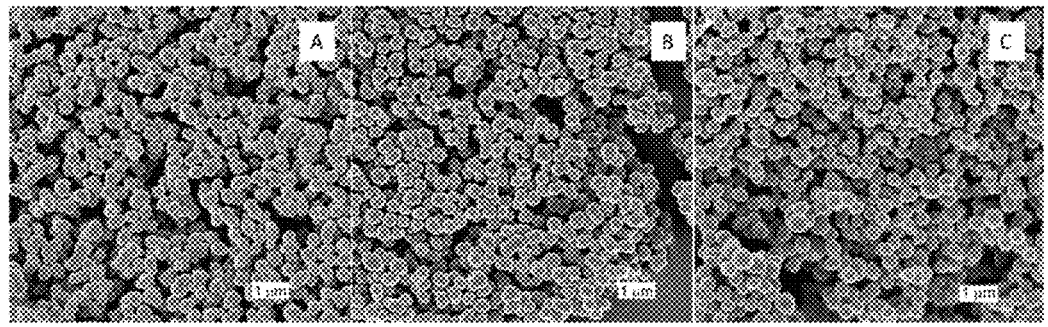
FIGS. 17A, 17B, and 17C are SEM images of P(GDMA-co-MMA) (10:3) microspheres formed at different monomer concentrations. (A) [GDMA]=62 mM, (B) [GDMA]=41.3 mM, (C), [GDMA]=20.7 mM (Table 1 entries 7-9, respectively).

Although a GDMA concentration of 83 mM lead to coagulation before 8 hours (trial 6), the reaction performed at GDMA concentration of 62 mM (trial 7) gave discrete polymer microparticles. SEM images showed that these particles had irregular morphologies similar to trials 1-5, albeit with smoother surfaces (FIG. 17A). Further lowering the monomer concentration afforded microparticles with spherical morphologies (trials 8 and 9, FIGS. 17B and 17C, respectively). DLS results for trials 7-9 showed the $D_h$ ranged from 730 to 833 nm with PDI values of 0.12-0.15, similar to what was observed for the microparticles formed at higher monomer concentrations. The diameter of the microspheres observed by SEM is significantly smaller than those determined by DLS. The difference is likely due to swelling of the microspheres in the presence of organic solvent, since DLS measurements were determined in THF while SEM was performed in the dry state.

Figure 18:
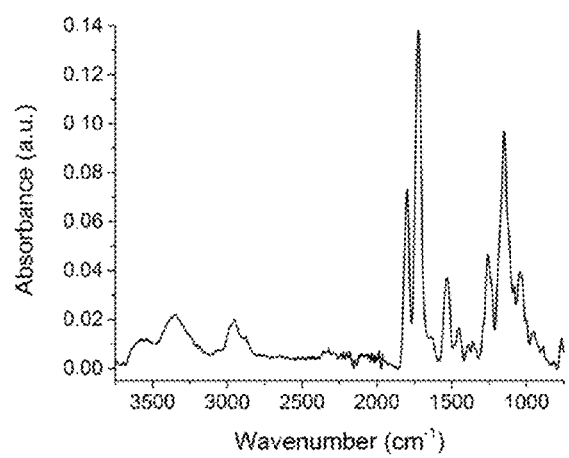
FIG. 18 shows the ATR-IR spectrum of the P(GDMA-co-MMA) microspheres.

FIG. 18 shows the ATR-IR spectrum of the P(GDMA-co-MMA) microspheres.

Thus, embodiments of MONOMERS, POLYMERS AND ARTICLES CONTAINING THE SAME FROM SUGAR DERIVED COMPOUNDS are disclosed. One skilled in the art will appreciate that the articles, devices and methods described herein can be practiced with embodiments other than those disclosed. The disclosed embodiments are presented for purposes of illustration and not limitation. One will also understand that components of the articles, devices and methods depicted and described with regard to the figures and embodiments herein may be interchangeable.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. For example, a conductive trace that "comprises" silver may be a conductive trace that "consists of" silver or that "consists essentially of" silver.

As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Use of "first," "second," etc. in the description above and the claims that follow is not intended to necessarily indicate that the enumerated number of objects are present. For example, a "second" substrate is merely intended to differentiate from another infusion device (such as a "first" substrate). Use of "first," "second," etc. in the description above and the claims that follow is also not necessarily intended to indicate that one comes earlier in time than the other.

A number of publications were referred to herein. Such publications may or may not be useful for aiding in obtaining a full appreciation of the subject matter disclosed. Each of the publications reference in this document is hereby incorporated herein by reference thereto in its respective entirety to the extent that it does not conflict with the disclosure presented herein.

The invention claimed is:

1. A compound of formula V below:

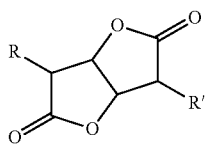

(V)

where R and R' are independently selected from the following:

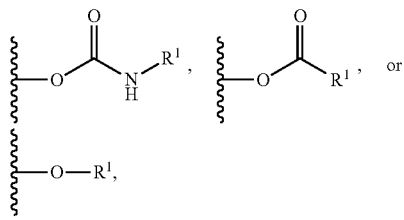

in which $R^1$ is independently selected from:

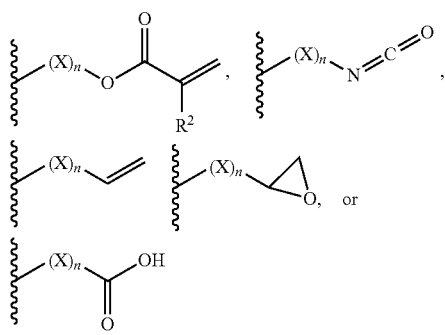

where X is a linking group;
n is an integer greater than or equal to 1; and
$R^2$ is hydrogen, or an alkyl.

2. The compound according to claim 1, wherein X is selected from hydrocarbons, esters and ethers.

3. The compound according to claim 1, wherein X is a $C_1$ to $C_6$ alkyl.

4. The compound according to claim 1, where R and R' are independently

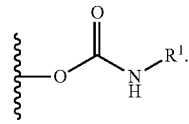

5. The compound according to claim 4, wherein $R_1$ is

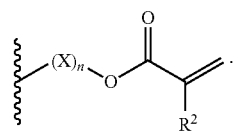

6. The compound according to claim 5, wherein $R^2$ is hydrogen or a $C_1$ to $C_3$ alkyl.

7. The compound according to claim 1 comprising glucarodilactone methacrylate (GDMA).

8. The compound according to claim 1 comprising mannarodilactone methacrylate (MDMA).

9. The compound according to claim 1 formed by reacting a sugar derived compound(s) comprising a lactone and two hydroxyls with a compound(s) comprising an isocyanate and an acrylate or methacrylate.

10. The compound according to claim 9, wherein the sugar derived compound comprises glucarodilactone, mannarodilactone, or a combination thereof.

11. The compound according to claim 9, wherein the compound comprising an isocyanate and an acrylate or methacrylate comprises 2-isocyanoethyl methacrylate (ICM).

12. The compound according to claim 9 comprising glucarodilactone methacrylate (GDMA).

13. The compound according to claim 9 comprising mannarodilactone methacrylate (MDMA).

14. A polymer formed by polymerizing at least a compound of formula V below:

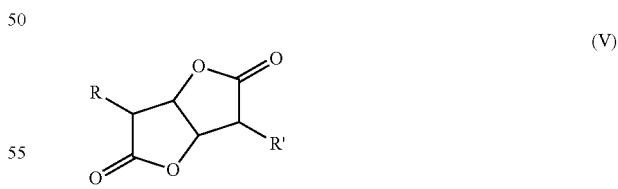

(V)

where R and R' are independently selected from the following:

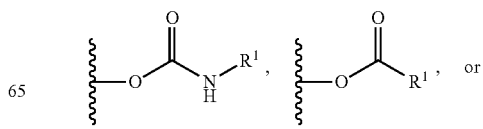

-continued

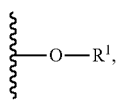

in which R¹ is independently selected from:

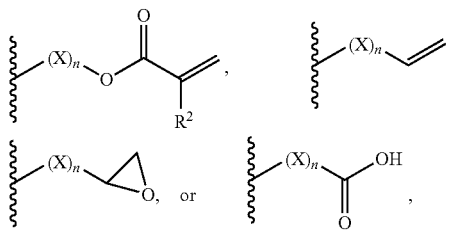

where X is a linking group;
n is an integer greater than or equal to 1; and
R² is hydrogen, or an alkyl.

15. The polymer according to claim 14, wherein X is selected from hydrocarbons, esters and ethers.

16. The polymer according to claim 14, wherein X is a $C_1$ to $C_6$ alkyl.

17. The polymer according to claim 14, where R and R' are independently

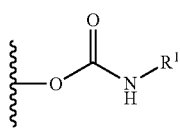

and $R_1$ is

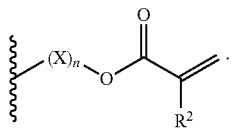

18. The polymer according to claim 14 wherein the compound according to formula V is glucarodilactone methacrylate (GDMA), mannarodilactone methacrylate (MDMA), or a combination thereof.

19. The polymer according to claim 14, wherein the polymer was formed from at least one monomer of formula V and a monomer not of formula V selected from:
urethane dimethacrylate (UDMA),
bisphenol A glycidyl methacrylate (bis-GMA),

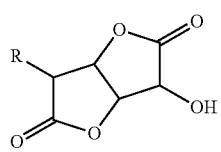

where R is selected from the following:

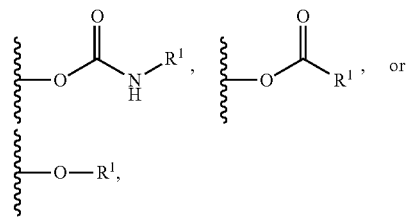

in which R¹ is independently selected from:

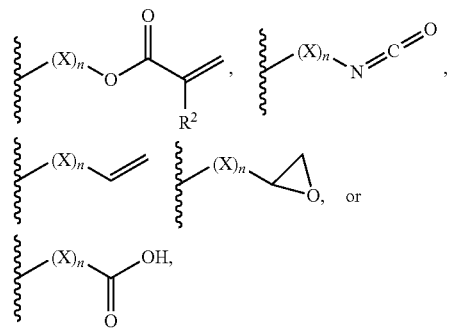

where X is a linking group;
n is an integer greater than or equal to 1; and
R² is hydrogen, or an alkyl,
and combinations thereof.

20. A drug delivery article comprising a polymer polymerized from a monomer of formula V

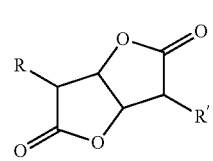

(V)

where R and R' are independently selected from the following:

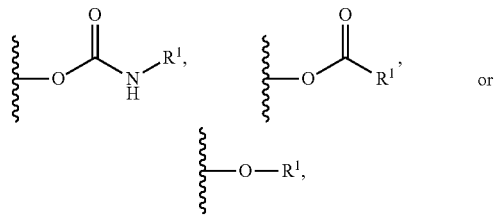

in which R¹ is independently selected from:

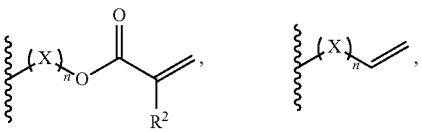

-continued
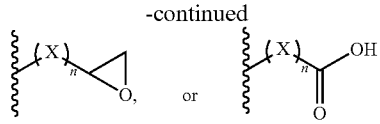
where X is a linking group;
n is an integer greater than or equal to 1; and
$R^2$ is hydrogen, or an alkyl.
* * * * *